United States Patent [19]

Jorgensen et al.

[11] Patent Number: 5,283,184

[45] Date of Patent: * Feb. 1, 1994

[54] GENETIC ENGINEERING OF NOVEL PLANT PHENOTYPES

[75] Inventors: Richard A. Jorgensen; Carolyn A. Napoli, both of Davis, Calif.

[73] Assignee: DNA Plant Technology Corporation, Mt. Kisco, N.Y.

[ * ] Notice: The portion of the term of this patent subsequent to Jul. 27, 2010 has been disclaimed.

[21] Appl. No.: 687,550

[22] Filed: Apr. 17, 1991

Related U.S. Application Data

[63] Continuation-in-part of Ser. No. 501,076, Mar. 29, 1990, and a continuation-in-part of Ser. No. 331,338, Mar. 30, 1989, Pat. No. 5,034,323.

[51] Int. Cl.$^5$ .................. C12N 15/29; C12N 15/82; A01H 4/00
[52] U.S. Cl. .................. 435/172.3; 800/205; 800/DIG. 67; 800/DIG. 12; 435/320.1; 935/30; 935/35; 935/64; 935/67
[58] Field of Search ............ PLT/82.1, 77, 80, 82.4; 800/200, 205, DIG. 67, DIG. 12; 435/172.3, 320.1; 935/35, 64, 67, 30

[56] References Cited

U.S. PATENT DOCUMENTS 5,034,323 7/1991 Jorgensen et al. ............ 435/172.3

FOREIGN PATENT DOCUMENTS 0218571 4/1987 European Pat. Off. .
0257993 3/1988 European Pat. Off. .

OTHER PUBLICATIONS

Niesbach-Klosgen et al. (1987) J. Mol. Evol. 26:213-225.
van der Krol et al. (Jun. 1988) Nature 333:866-869.
van der Krol et al. (1990) Plant Molecular Biology 14:457-466.
Meyer, et al. (1987) Nature 330: 677-678.
Fillati, et al. (Jul. 1987) Bio/Technology 5:726-730.
Martin; et al. (1985) The EMBO Journal 4(7):1625-1630.
Reif, et al. (1985) Mol. Gen. Genet. 199:208-215.
Reeves et al., (1986) Gen. and Cytogen., Biol. Abstr. 83(2): AB-454-455, 13846 (1986).
Krishnan et al. (1986) Plant Phys. Biochem. and Biophy., Biol. Abstr. 82(7):AB-855, 67053.
Hansen (1987) Carlsberg Res. Commun., 52:381-392.
Scherer et al. (1987) Plant Mol. Biol. 9:127-134.
Horsch et al. (1985) Science, 227:1229-1231.
Hall et al. (1987) New Phytologist, 103:33-43.
Mol et al. (1983) Mol. Gen. Genet. 192:424-429.
Forkmann et al. (1979) Planta, 144:189-192.
Dunsmuir et al. (1987) Plant Biotechnology (T. Mabry, Ed.) IC2 Institute, 107-119.
Martin et al. (1985) EMBO J., 4:1625-1630.
Van Tunen et al. (1988) EMBO J., 7:1257-1263.
Spribille et al. (1982) Planta, 155:176-182.
Koes et al. (1987) Plant Mol. Biol., 10:159-169.
Koes et al. (1986) Nucleic Acids Res., 14:5229-5239.
Reimold et al. (1983) EMBO J., 2:1801-1805.
Kreuzaler et al. (1983) Proc. Natl. Acad. Sci. USA, 80:2591-93.
Fillatti et al. (1987) Bio/Technology 5:726-730.
Wiering et al. (1984) "Genetics of Flower and Pollen Colors" in Petunia, Monographs on Theoretical and Applied Genetics, vol. 9 (K. C. Sink, Ed.), Springer Verlag, Berlin.
Martin et al. (1987) "The Control of Floral Pigmentation in Antirrhinum Majus" in Developmental Mutants in Higher Plants, (Thomas & Grierson, Eds.) Cambridge University Press.
Harborne (1976) "Functions of Flavonoids in Plants" in Chem. and Biochem. of Plant Pigments (T. Goodwin, Ed.) 2nd Ed., vol. 1, Academic Press, London, p. 737.
Hahlbrock (1981) "Flavornoids" in the Biochem. of Plants (E. Conn, Ed.) vol. 7, Academic Press.
Ozeki et al. (1987) Physiologia Plantarum, vol. 69, 128.
Promega 1988/89 Catalog (Wisconsin, U.S.A., page 2).

Primary Examiner—Che S. Chereskin
Attorney, Agent, or Firm—Townsend and Townsend Khourie and Crew

[57] ABSTRACT

Methods are provided for producing plants exhibiting one or more desired phenotypic traits. In particular, transgenotes are selected that comprise a DNA segment operably linked to a promoter, wherein transcription products of the segment are substantially homologous to corresponding transcripts of endogenous flavonoid biosynthetic pathway genes.

31 Claims, 4 Drawing Sheets

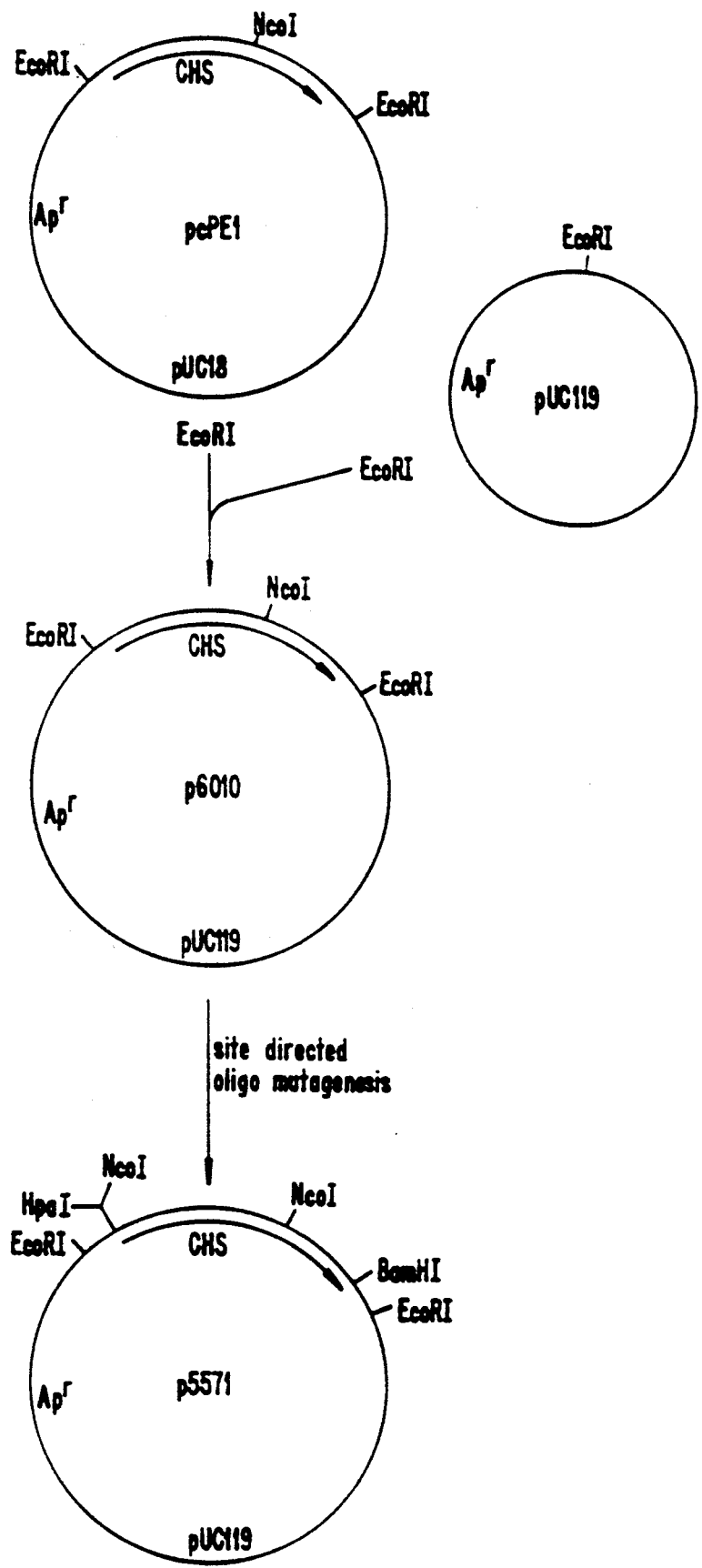
FIG._1A.

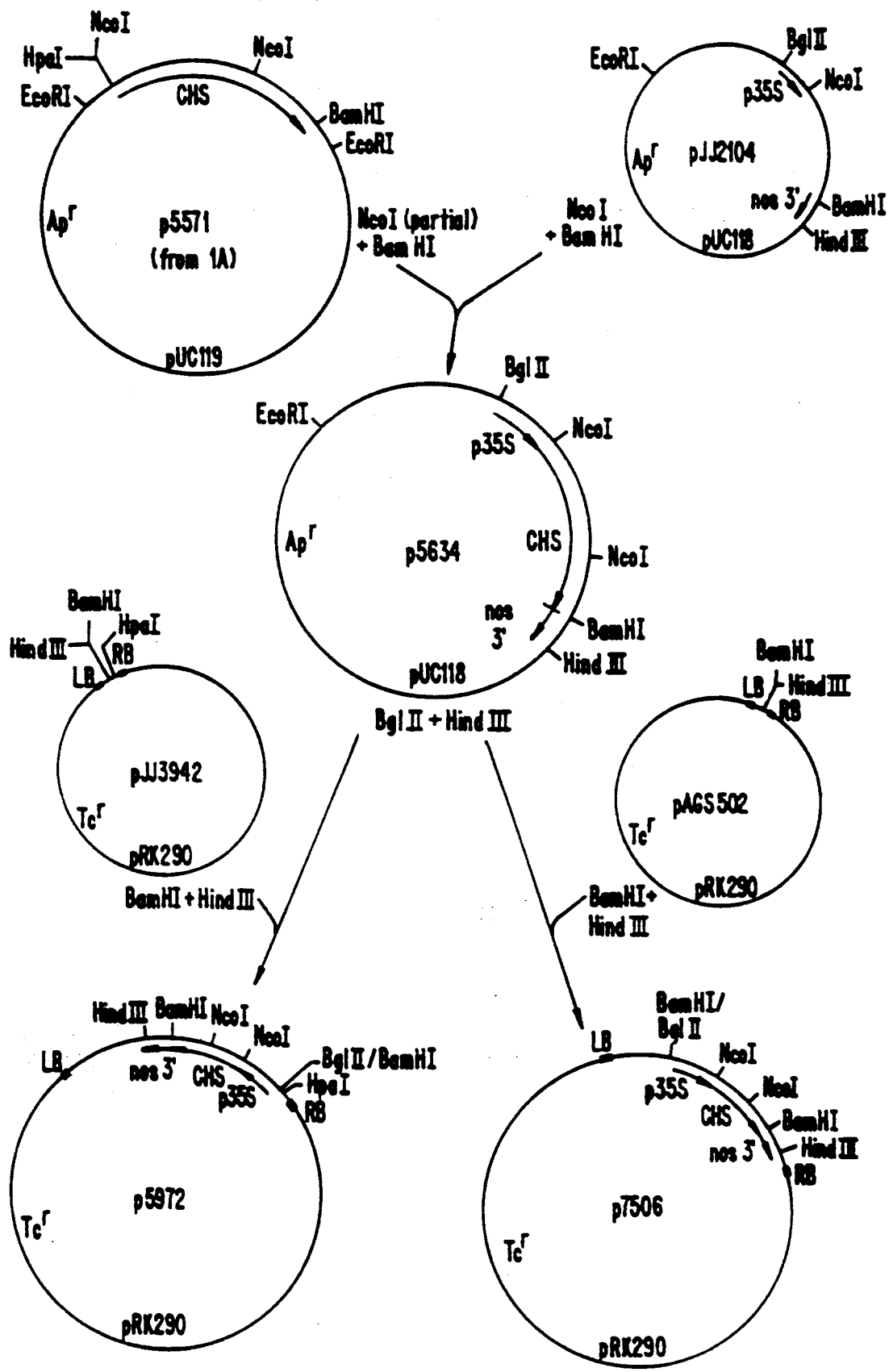
FIG._1B.

GENETIC ENGINEERING OF NOVEL PLANT PHENOTYPES

CROSS-REFERENCE TO RELATED APPLICATIONS

This application is a Continuation-in-part of U.S. Ser. No. 07/501,076, filed Mar. 29, 1990, and claims priority from PCT application no. US89/03565 filed Aug. 18, 1989 and U.S. Ser. No. 07/331,338 filed Mar. 30, 1989, now U.S. Pat. No. 5,034,323.

FIELD OF THE INVENTION

This invention relates generally to the use of recombinant DNA methods for genetically altering plants, and more particularly, to improved means for altering plant phenotypes, such as color patterns and color intensity of flowers and other plant parts.

BACKGROUND OF THE INVENTION

Controlling metabolic pathways in plants has long been a goal of horticulturists. See, e.g., Bonner and Varner (1976) *Plant Biochemistry*, Academic Press, New York, which is incorporated herein by reference. The advent of recombinant DNA technology has provided new approaches to reaching that goal. While significant progress has been made in understanding gene regulation, control of plant gene regulation remains at a relatively early state of development.

The water soluble pigment flavonoids are significant in their contribution to the coloration and other properties of higher plants. For example, the flavonoids are responsible for most orange, scarlet, crimson, mauve, violet and blue colors, and contribute significantly to yellow, ivory and cream colored flowers. See, Harborne, (1976) *Chemistry and Biochemistry of Plant Pigments*, 2d ed., Goodwin (Ed.) Acad. Press, London. The most important of the pigment molecules are the anthocyanins, particularly pelargonidin, cyanidin and delphinidin. These are the darker colored pigments responsible for the orange-red, magenta and mauve colors, respectively. The other major flavonoid types, the chalcones, isomeric flavanones, flavones and flavonols are light colored and tend to have relatively smaller effects on intensity or patterns of color.

The functions of these pigments extend well beyond coloration of flowers, however. The pigments also color fruits, leaves and other plant parts, and importantly provide plants with UV protection, as well as protection against herbivores and microbes. Other uses include allelopathy and even some pharmaceutical applications.

The biosynthetic pathways of these various pigments have been extensively studied in many different plant species. The chalcones and aurones are products requiring only the initial biosynthetic enzymes, being direct products of the earliest precursors. The flavones and flavonols are intermediate, and the anthocyanins are products requiring substantial modifications from the initial precursors. All of these products are dependent upon the activity of the initial enzyme chalcone synthase (CHS), which catalyses the production of chalcone from three molecules of malonyl-Coenzyme A and one molecule of coumaroyl-Coenzyme A.

Essentially, all of these phenotypic traits have naturally evolved coordinately with constraints related to plant reproduction. For example, the appearance of a flower has generally resulted from the requirement to attract insects who assist in the pollination process essential for the sexual reproduction of the higher plants. Of course, the decorative and ornamental features impart to flowers a significant commercial value.

Mankind has traditionally intervened in some of the natural processes by, e.g., simply selecting particular flower colors and patterns which might otherwise not have survived in nature. Breeders routinely generate new and unusual flower phenotypes by a variety of time-tested breeding methods. The classical techniques for breeding improved plants, such as different flower varieties with altered flower color intensities or color patterns, typically required natural genetic variability within the experimental gene pool of the species and its relatives. More recently, the generation of variability by induction of mutations has been utilized. Breeders then select among the resulting population those products exhibiting interesting phenotypes, for further characterization.

Unfortunately, the induction of mutations to generate diversity often involves chemical mutagenesis, radiation mutagenesis, tissue culture techniques, or mutagenic genetic stocks. These methods provide means for increasing genetic variability in the desired genes, but frequently produce deleterious mutations in many other genes. These other traits may be removed, in some instances, by further genetic manipulation (e.g., backcrossing), but such work is generally both expensive and time consuming. For example, in the flower business, the properties of stem strength and length, disease resistance and maintaining quality are important, but often initially compromised in the mutagenesis process.

As noted, the advent of recombinant DNA technology has provided horticulturists with additional means of modifying plant genomes. While certainly practical in some areas, to date genetic engineering methods have had limited success in modifying the flavonoid biosynthetic or other pathways. Recently, the inhibition of flower pigmentation with a constitutively expressed "anti-sense" chalcone synthase gene has been reported (Van der Krol et al., (1988) Nature 333:866–869).

Thus, there exists a need for improved methods for producing plants with desired phenotypic traits. In particular, these methods should provide general means for phenotypic modification, and may lessen or eliminate entirely the necessity for performing expensive and time-consuming backcrossing.

SUMMARY OF THE INVENTION

In accordance with the present invention, methods and compositions are provided for producing plants exhibiting one or more desired phenotypic or genotypic traits. The invention is based in part on the surprising discovery that plants exhibiting desired trait(s) can be selected from transgenotes comprising a nucleic acid segment operably linked to a promoter, wherein transcription products of the segment are substantially homologous to corresponding transcripts of an endogenous gene. The transgenotes are grown into plants, such as flowering plants capable of exhibiting novel traits, including a reduction in color intensity, an altered pattern color, or a change in basic color of the plant flowers or other plant organs.

The invention further embraces the introduction of one or more metabolic enzyme gene regions, e.g., flavonoid biosynthetic pathway gene regions, under the control of promoter regions (either native or heterologous), into dicots and other plants in which the gene is endogenous. In particular, the invention comprises plants, such as those of the genera Petunia and Chrysanthemum, wherein the plant is grown from a cell transformed with a sequence which is transcribed into an RNA sequence substantially homologous (other than anti-sense) to a desired gene. In a preferred embodiment the gene is a flavonoid biosynthetic pathway gene. DNA or RNA equivalents are introduced into plants in a way to produce more of the endogenous (already present) transcript, but not to produce solely an anti-sense transcript. This is preferably accomplished by using a DNA segment (natural or constructed) in which the promoter is positioned in the normal orientation at the 5' end of the encoding region so that a "sense" transcript (rather than antisense transcript) will be produced. The plant cells can be transformed with a variety of vectors, such as viral vectors, episomal vectors, shuttle vectors, Ti plasmid vectors and the like, all in accordance with well known procedures.

The invention also embraces methods for reducing expression of endogenous nucleic acid sequences coding for proteins acting in various biosynthetic or other enzyme pathways, such as the flavonoid biosynthetic pathway of a plant, the method comprising the step of introducing into a cell of the plant a DNA sequence substantially homologous to the endogenous sequence and under the operational control of a promoter sequence, such as a cauliflower mosaic virus sequence. The DNA segment will be sufficient to introduce the repression effect into the plant and typically comprises at least about 50 nucleotides but may be a full length gene. In addition, the invention comprises the methods of preparing and using the various DNA constructs of the present invention.

BRIEF DESCRIPTION OF THE FIGURES

FIG. 1A shows the constructions of p5571.

FIG. 1B shows the construction of p5972 and p7506.

DETAILED DESCRIPTION

Figure 2:
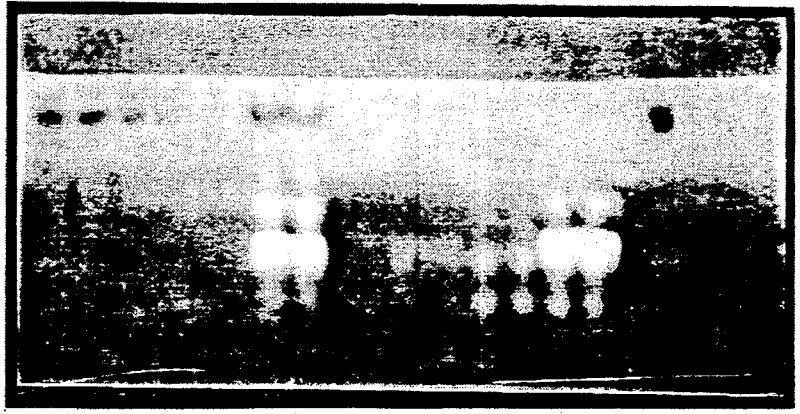
FIG. 2. Flavonoid extracts of petunia corollas chromatographed on crystalline cellulose chromatography places in Forestal solvent (acetic acid: conc. HCL: water, 30:3:10). Lanes: 1,2- 21838; 3,4- 21841; 5,6- W80; 7,8-V26; 9,10- W37; 11,12- W85; 13,14- R77; 15,16-R27; 17-caffeic acid; 18- coumaric acid. The plate was photographed using UV light from below, and photographed with a red filter. Anthocyanins and coumaric acid can be detected readily this way, but caffeic acid and flavonols are not detected well.

The present invention provides novel methods for producing plants, and embraces the plants so produced, and methods of their use. The invention is based in part on the discovery that a reduction in expression (i.e., repression) of a cellular gene product may be attained upon introduction into the cell of a nucleic acid fragment, e.g., a flavonoid biosynthetic pathway gene sequence, that is ultimately transcribed to yield a mRNA transcript substantially homologous to a portion of the gene's transcript. The introduced transcript is preferably produced prior to native transcript (if any), but may be produced simultaneously with native transcript production. Depending on the time and amount of transcript produced in a transgenote, a plant grown from it will exhibit a variety of different phenotypic traits. In particular, selecting plants with varying phenotypes, for instance color patterns and intensity, typically without harming other desirable plant characteristics, can be readily achieved in accordance with the present invention.

By way of example, and not limitation, an exemplary preferred embodiment of the present invention entails introducing a full-length chalcone synthase (CHS) coding sequence in an orientation which would be operably linked to a cauliflower mosaic virus promoter into *Petunia hybrida* cells. These transgenotes are grown into plants and variations in flower coloration are selected. The modified flowers exhibit substantially all of the characteristics of the native *Petunia hybrida* plants. In another aspect of the present invention, those skilled in the art will readily appreciate that additional traits (i.e., other than proteins in the flavonoid biosynthetic pathway), additional plant nucleic acid sequences and the like may be readily substituted in accordance with the following guidelines.

Traits

A variety of traits are selectable with appropriate procedures and sufficient numbers of transgenotes. Such traits include, but are not limited to, visible traits, environmental or stress related traits, disease related traits, and ripening traits. The repressive effect is applicable to a variety of genes expressed in plants including, for example, genes responsible for the synthesis or metabolism of peptides, proteins, fatty acids, lipids, waxes, oils, starches, sugars, carbohydrates, flavors, odors, fragrances, toxins, carotenoid pigments, hormones, cell wall polymers, gene regulatory molecules, flavonoids, storage proteins, phenolic acids, coumarins, alkaloids, quinones, lignins, glucosinolates, tannins, aliphatic amines, celluloses, polysaccharides, glycoproteins and glycolipids.

For instance, an alteration in the production of fatty acids or lipids can be engineered (and fatty acid composition of, e.g., an oil-producing plant thus altered) by blocking synthesis of a specific chain elongation or desaturation enzyme. Also, the synthesis of starch can be reduced and sugars accumulated (and sugar content of, e.g., an edible plant thus altered) by blocking an enzyme required for starch synthesis. Similarly, fragrant molecules can be released from cells (thus altering the scent characteristics of, e.g., ornamental flowers) by blocking the enzymes responsible for glycosylation of such molecules.

Among the easiest to select are the flavonoid genes, giving rise to visible traits. In particular, the traits of color intensity, color hue and color pattern are subject to the repression effect.

In addition to variation for color amongst flowers, there is also variation amongst white colored flowers for the block in the flavonoid biosynthetic pathway. For example, in petunia there are mutations which block the pathway at the dihydroflavonol synthase step, so that dihydroflavonols and flavonols accumulate in the flowers (Beld et al., 1989, Plant Mo. Biol., 13, 491–502, which is incorporated herein by reference). In snapdragon, there are mutations which block the pathway at the chalcone synthase step, so that precursors to these reaction accumulate (for example, caffeic or coumaric acids). In both snapdragon and petunia, mutations at the flavanone-3-hydroxylase step lead to the accumulation of naringenin, resulting in white flowers (e.g., Froemel et al., 1985, Theor. Appl. Gent., 70, 561). By such analysis of the accumulated intermediates in white flowers, it is possible to assess the point at which flavonoid biosynthesis has been blocked.

The class of genes within the flavonoid biosynthetic pathway includes those nucleic acid sequences directly involved in reactions or control of reactions which synthesize or modify a flavonoid compound. Flavonoids are a class of compounds, numbering about 3000 whose functions in plants include coloration in flowers, fruits, leaves, and other organs. Examples of flavonoid biosynthetic genes include those for chalcone synthases, chalcone isomerases (CHI), flavanone 3-hydroxylases, dihydroflavonol reductases, flavanone 2-hydroxylases, dihydroflavanol 2-hydroxylases, flavonoid 3'-hydroxylases, flavonoid 5'-hydroxylases, flavonoid glycosyl-transferases (including glucosyl transferases such as UDPG: flavonoid 3-O-glucosyl transferase and UDPG: flavonol 7-O-glucosyl transferase, and rhamnosyl transferases), flavonoid methyltransferases (such as SAM:anthocyanidin 3-(p-coumaroyl)-rutinoside-5-glucoside 3',5'-O-methyltransferase) and flavonoid acyltransferases. See, Hahlbrock (1981) *Biochemistry of Plants*, Vol. 7, Conn (Ed.); Weiring and de Vlaming (1984) "Petunia", K. C. Sink (Ed.), Springer-Verlag, New York. By way of example of the components of these pathways, phenylalanine is converted to cinnamic acid; cinnamic acid is converted to caffeic acid (in a side branch) and to coumaryl-coenzyme A; coumaryl-coenzyme A is converted with chalcone synthase to a tetrahydroxy chalcone; the tetrahydroxy chalcone is converted with chalcone isomerase to naringenin; and naringenin is converted in a subsequent series of steps to anthocyanins. Blockage or inactivation at a given stage leads to build-up of precursors and side chain products of precursors. For instance, blockade at the chalcone synthase stage leads to build-up of coumaric acid and caffeic acid.

Anthocyanin pigmented flowers have colors throughout the range orange to red to purple to blue. Chalcones and aurones are yellow or orange. Flavones and flavonols are very light yellow, or "cream" colored. Flavanones are colorless. Elimination of anthocyanins and diversion of the pathway to flavone or flavonol production would create cream colored flowers. Shifts from blue to purple or purple to red or red to orange can be engineered by interfering with 3' or 5' hydroxylases of 2-hydroxylases. Interference with 2-hydroxylases can also reduce color intensity of anthocyanin pigmented plants. Interference with CHS would create white flowers and with chalcone isomerase would create yellow flowers. A wide variety of bi-color patterns can be created, the two colors being the color of the target plant before engineering and the color resulting from the expression of the introduced flavonoid gene. Types of patterns include: radial star-like patterns; picotee (white outer edge); white annular center; concentric colored rings; erratic, irregular patterns, e.g., variegated or blotchy. There are many variations on these patterns, some more attractive than others, some with sharp boundaries between colors, some with diffuse boundaries, some with linear boundaries, some with wavy, curved boundaries. Also lighter, solid colors are observed.

The present invention is also applicable to generate plants exhibiting modified absolute levels or relative proportions of various oil products. In particular, genes encoding enzymes involved in lipid metabolism may be used, in the methods described, to modify metabolism of oils and other lipids, such as fats. The oils are lipids which typically are liquid at room temperatures and typically will have various unsaturations in the fatty acid components and shorter lipid chains than the fats. See generally, Lehninger (1978) *Biochemistry* (2d Ed), Worth Publishers, New York; and Bonner and Varner (1976) *Plant Biochemistry* (3d Ed), Academic Press, New York. Much is also known about the applicable biosynthetic pathways at the genetic level. See, e.g., the following, and references cited therein: Shure et al. (198), *Cell* 35:225-233; Preiss et al., *Tailoring Genes for Crop Improvement* (Bruening et al., eds.), Plenum Press (1987), 133-152; Gupta et al. (1988), *Plant Mol. Biol.* 10:215-224; Olive et al. (1989), *Plant Mol. Biol.* 12:525-538; and Bhattacharyya et al. (1990), *Cell* 60:155-122, all of which are incorporated herein by reference.

Genes encoding various enzymes found in the pathways for production of oils are introduced into a target plant to alter the expression of important endogenous genes. The relative proportions or absolute content of various different types of oils may be thereby altered, and using information known in the art about sugar-starch biosynthetic pathways at the genetic level (see, e.g., citations on same above). Various enzymes of particular interest would include, among others, stearyl desaturase, acetyl transacylase, malonyl transacylase, $\beta$-ketoacyl ACP-synthetase, $\beta$-keto ACP-reductase, enoyl ACP-hydrase, acyl-ACP thioesterases and enoyl ACP-reductase.

The present invention is also applicable to the alteration of sugar metabolism or carbohydrate metabolism in plants. For example, genes encoding enzymes used in carbohydrate metabolism, e.g, in the metabolism of amylose, pectins, cellulose and cell walls, are used to regulate enzymatic expression and activity to modify sizes of pools of metabolic intermediates or kinetics of conversion, thereby changing the starch or sugar contents of various plants.

Genes encoding various enzymes in carbohydrate metabolism may be introduced into a target plant to alter the expression of various enzymes in the pathways. Various enzymes of particular interest in carbohydrate metabolism include phosphorylase, starch synthetase, Q-enzyme, sucrose-6-phosphate synthetase, sucrose-6-phosphate phosphatase, ADP-glucose pyrophosphorylase and various amylases. See generally, Bonner and Varner (Eds) (1976) *Plant Biochemistry* (3d ed.), Academic Press, New York. Much is also known about the applicable biosynthetic pathways at the genetic level. See, e.g., the following, and references cited therein: Stefansson et al. (1961), *Can. J. Plant Sci.* 41:218-219; Knowles et al. (1972), *Oil Crops of the World* (Robbelen et al., eds.), McGraw-Hill, 260-282; Hammond et al. (1983), *Crop Sci.* 23:192-197; Widstrom et al. (1984), *Crop Sci.* 24:1113-1115; Green et al. (1984), *Euphytica* 33:321-328; Graef et al. (1985), *Crop Sci.* 25:1076-1079; Somerville et al., *Recent Advances in Phytochemistry* (Conn, ed.), Plenum Press (1988), 19-44; Kunst et al. (1988), *PNAS U.S.A.* 85:4143-4147; and, Browse et al., "Strategies for Modifying Plant Lipid Composition" (1989), *Plant Gene Transfer* (Lamb, C. et al., eds.), Alan R. Liss, all of which are incorporated herein by reference.

Suitable sources for gene sequences usable in accordance with the present invention are plants, in particular higher plants. For example, virtually all of higher plants normally possess a flavonoid biosynthetic pathway of some type. In particular, any flavonoid pathway which generates naringenin chalcone or compounds generated from naringenin chalcone which itself is generated from coumaroyl-Coenzyme A and malonyl-Coenzyme A by chalcone synthase will be appropriate.

Introduced Nucleic Acid Sequences

The properties of the nucleic acid sequences are varied, and the preferred embodiments will describe a number of features which the person of skill in the art may recognize as not being absolutely essential, but clearly advantageous. These include isolation methods of the particular sequence to be introduced, certain features of the sequence and certain features of the associated vector, if any. Transcriptional expression of the introduced gene is generally important, and—without intending to be limited to a particular mechanism—additional production of a transcript relative to the normal expression of the endogenous form of the sequence is likely part of the underlying mechanism, especially prior to attainment of peak levels of endogenous gene expression. However, other mechanisms may be involved, for instance, mere physical presence of exogenous copies of these genes, e.g., in higher copy numbers or integrated into particular genetic locations, may contribute to the repressive effect.

RNA resulting from transcription shall be referred to herein on occasion as "transcript" or in some instances "mRNA". Typically, transcript which is processed (e.g., introns removed and 3' end polyadenylated) is referred to as mRNA ("messenger"). As used herein "homologous" means corresponding to (the same as). For example, RNA which is homologous to a gene, is RNA which corresponds to the coding strand sequence (with the normal exception of uracil for RNA in place of thymidine for DNA). Thus, cellularly produced "homologous mRNA", as used herein, is complementary to the template DNA strand of the gene.

mRNA may contain "coding regions" of codon triplets which encode for translation into amino acids making up the polypeptide. A primary transcript may contain both exons (typically containing the coding regions) and introns, the latter of which are often excised prior to translation.

Expression of an endogenous gene, e.g., a gene in the flavonoid pathway, yields varying levels of transcript depending on the type of cell and its developmental stage. During flower development, certain cells, e.g., cells that give rise to petal epidermal tissue, produce or begin to produce a transcript at a level which rises at or subsequent to flower meristem initiation. The transcript level reaches a peak later in flower development and eventually decreases. This rise and fall of transcript level may occur over a series of days, e.g., 7-14 days. The rise may also occur rapidly, e.g., over a period of hours, especially in the event of induction such as by UV or visible light (see, Mol et al., (1983) *Mol. Gen. Genet.* 192:424-429, which is incorporated herein by reference), particularly under natural summer light conditions (or the artificial equivalent thereof). For example, the transcript level is usually decreasing at the mature flower stage (flower maturation).

One proposed mechanism of repression would require that some transcription of the introduced sequence be produced, e.g., transcription of introduced DNA homologous to transcribed endogenous DNA (although transcription of introduced DNA homologous to untranscribed endogenous DNA may also be involved). Specifically, however, observed genes' endogenous transcription levels dropped about 50-fold in comparison to native conditions. The introduced genes' transcript levels were also low with respect to the endogenous genes' levels, but the total was also lower. While the introduced sequence need not necessarily correspond to the final translated message or a part thereof, there are likely corresponding forms of the mRNA which are functional in repression, but still contain parts of introns or only non-translated segments of the primary transcript of the normal endogenous sequence. Thus, the effect may occur where the introduced sequence contains no coding sequence per se, but only intron or untranslated sequences substantially homologous to sequences present in the primary transcript of the endogenous sequence. Also, while the present invention is not necessarily tied to any specific mechanism, the mechanism may involve methylation of both the introduced and the endogenous homologous sequences (methylation is known to be able to spread from a sequence to adjacent sequences).

The introduced sequence generally will be substantially homologous to the endogenous sequence intended to be repressed, such that the controlling elements recognize that the introduced sequence is present, the interaction results in the repressive effect. This minimal homology will typically be greater than about 65%, but a higher homology might exert a more effective repression of expression of the endogenous sequences. Substantially greater homology, or more than about 80% is preferred, though about 95% to absolute identity would be most preferred. Consequently, the effect should apply to any other proteins within a similar family of genes exhibiting homology or substantial homology. For example, the chalcone synthase protein may be encoded by one or more homologous genes which comprise the chalcone synthase gene family, and repression of one member of the family will typically serve to impose the same repressive effect on others of the family. Similarly, for example, chalcone synthase genes from other plant species may be utilized.

The introduced sequence, needing less than absolute homology, also need not be full length, relative to either the primary transcription product or fully processed mRNA. In this regard and in accordance with the present invention, transformation of partial or truncated genes also inhibits expression. Specifically, transformants of a tobacco plant with an 860 base pair fragment containing approximately the first two-thirds of a wild-type nopaline synthase gene under control of the CaMV 35S promoter showed suppression of the wild-type nos gene previously transformed into the tobacco Caltivar (see, Goring et al., *Proc. Natl. Acad. Sci. U.S.A.,* 88:1770-1774, at 1771 (1991), which is incorporated herein by reference). Similarly, tomato plants transformed with a 730 bp fragment (about 678 bp of coding sequence, representing about 51% of the total length; i.e., 1382 bp coding sequence plus 52 bp at 5' end) from a polygalacturonase (PG) cDNA (Grierson, et al., *Nucl. Acids. Res.* 14:8595-8603 (1986)) under the control of the CaMV 35S promoter showed inhibition of the endogenous PG gene during ripening (see, Smith, et al., *Mol. Gen. Genet.,* 224(3):477-481, at 478 (1990), which is incorporated herein by reference).

A higher homology in a shorter than full length sequence compensates for a longer less homologous sequence. Furthermore, the introduced sequence need not have the same intron or exon pattern, and homology of non-coding segments will be equally effective. Normally, a sequence of greater than 50-100 nucleotides should be used, though a sequence of greater than about 200-300 nucleotides would be preferred, and a sequence of greater than 500-1000 nucleotides would be especially preferred depending on the size of the endogenous gene.

It should be noted that since a full length coding sequence is unnecessary, it is possible to produce the same effect on multiple proteins using a single transformation by fusing multiple sequences together to coordinately repress various different genes. Assuming a sufficient number of introductions are made, the introduced sequence need not be linked to an operative promoter sequence. However, a promoter sequence would be preferred, particularly a partially or fully constitutive promoter. "Operably linked" refers to functional linkage between the affecting sequence (such as a promoter or 3' segments) and the controlled nucleic acid sequence. The same effect would be produced by the introduction of a promoter operably linked to the coding strand of an endogenous sequence. This can be effected by either the introduction of a promoter alone to a site operably linked to the target sequence, or by the reintroduction of a sequence of endogenous origin recombinantly attached to an operably linked promoter (resulting in a chimeric gene).

A heterologous sequence is one that originates from a foreign species, or, if from the same species, is substantially modified from its original form.

In considering the expected temporal stage of expression of the introduced gene, relevant factors include the type of promoter, the temporal pattern of the promoter, and the operation of the promoter in view of its position within the genome. A promoter which is expressed concurrently with or prior to the normal activation of the homologous endogenous sequence is preferred. A constitutive promoter is most preferred, such as the cauliflower mosaic virus promoter. This promoter is constitutive because its operation is relatively independent of the developmental stage of the cell in which it is contained. A regulated promoter, such as ones associated with the ribulose-1,5-bisphosphate carboxylase, the chlorophyll binding proteins or the glycine-rich root protein genes are also suitable. This control may be either temporal with respect to the developmental stage of the cell, or based upon differential expression by different parts or organs of the plant.

As referred to above, the operation of a promoter may vary depending on its location in the genome. Thus, a regulated promoter may operate differently from how it does in its normal location, e.g., it may become fully or partially constitutive.

It is preferred to have the DNA sequence linked to and situated at a distance from the promoter corresponding to the distance at which the promoter is normally most effective so as to ensure sufficient transcriptional activity. This distance should be within about 1000 nucleotides, preferably within about 500 nucleotides and more preferably within about 300 nucleotides of the translation initiation codon.

At the 3' end of the coding sequence, operably linked segments may also be included. Thus, it would be optimum to have a 3' untranslated region containing the polyadenylation site and any relevant transcription termination sites. A 3' sequence of less than about 1000 nucleotides is sufficient, about 500 preferred and about 300, or the length of the 3' untranslated tail of the endogenous sequence is more preferred.

If the introduced gene is an intact gene from the target plant or other plant species (meaning a complete gene containing coding sequences, intron, promoter, enhancers and other cis-acting regulatory elements either upstream (5') or downstream (3') of the coding sequences), a fraction of independent transgenotes, depending on the gene, may carry the introduced gene in locations that result in abnormal expression, i.e., expression at abnormal times in development. If the introduced gene is a chimeric gene (meaning that one or more elements, such as a promoter, from another gene has been substituted for a component of the intact gene or added to the intact gene, including coding sequences fused to upstream and downstream sequences necessary or beneficial for expression) and is driven by a constitutive (fully or partially) promoter, then abnormal levels and times of expression will be achieved in a large fraction of transgenotes. If the introduced gene is a chimeric gene and is driven by a developmentally regulated promoter, depending on the promoter, some fraction of transgenotes will show abnormal levels and times of expression of the introduced gene. The strength of the promoter or other cis element can be the same, lower, or higher than the coding sequence's usual promoter. The timing in development can be earlier or the same.

While many of these improvements suggested are not essential, the efficiency of production of useful transgenotes may be significantly affected. Some of the transgenotes may be identical to the parental plants, others may have reduced amounts of colored or colorless flavonoids throughout the petals or other organs of interest. Others may have reduced amounts of flavonoids in certain cells or patches of cells or segments of petals or other organs resulting in regular or irregular patterns. Flowers on the same plant may even have different patterns. The likelihood of obtaining a desirable transgenote will depend upon the number of transgenotes screened and the efficiency of actual transformation and expression of the foreign nucleic acid sequence. Typically, at least about 25 to 50 transgenotes will be screened, but 100 to 500 or more may need to be screened before the described effect is seen.

The choice of nucleic acid to exert the described repressive effect is broad. Assuming appropriate selection procedures and sufficient numbers of transgenotes, a wide variety of plant genes could display this effect. For example, genes responsible for the synthesis or metabolism of peptides, proteins, fatty acids, lipids, waxes, oils, starches, sugars, carbohydrates, flavors, odors, fragrances, toxins, carotenoid pigments, hormones, cell wall polymers, gene regulatory molecules, flavonoids, seed storage proteins, phenolic acids, coumarins, alkaloids, quinones, lignins, glucosinolates, tannins, aliphatic amines, celluloses, polysaccharides, glycoproteins and glycolipids and particularly genes associated with plant pigmentation. Among the plant pigmentation genes are the flavonoid genes, and most particularly the chalcone synthase gene sequence.

These gene sequences may be isolated by standard procedures of hybridization of genomic or cDNA libraries by the methods described in Maniatis et al. (see below). Screening may be by (1) nucleic acid hybridization using homologous genes from other organisms, (2) probes synthetically produced to hybridize to particular sequences coding for known protein sequences, or (3) DNA sequencing and comparison to known sequences. Sequences for specific genes may be found, e.g., in GenBank, National Institutes of Health computer data-base), or may be determined after isolation, typically using techniques as described.

Flavonoid genes, for example, may be enriched in libraries by differential hybridization which requires that the mRNA of the target genes be expressed more abundantly in one tissue than in another. Labelled RNA or cDNA from each tissue is hybridized to replicas of the library and tissue specific clones are identified and isolated. Screening can then be used to identify the target gene among the set of tissue specific genes (Kreuzaler et al., (1983) *Proc. Natl. Acad. Sci. U.S.A.* 80:2591-2593).

Antibody screening of expression libraries with antibodies made against homologous proteins can select nucleic acid sequences which would code for homologous functions. Selection of sequences homologous to a known flavonoid biosynthetic pathway protein will enable isolation of other forms or equivalent forms from different sources.

Transposon tagging can assist in the isolation of the relevant gene. Transposon tagging typically involves a mutation of the target gene. A mutation is isolated in which a transposon has inserted into the target gene and altered the resulting phenotype. Using a probe for the transposon, the mutant gene can be isolated. Then, using the DNA adjacent to the transposon in the isolated mutant gene as a probe, the normal wild type allele of the target gene can be isolated (McLaughlin and Walbot (1987) *Genetics* 117:771-776; Dooner et al., (1985) *Mol. Gen. Genetics* 200:240-246; and Federoff et al., (1984) *Proc. Natl. Acad. Sci. U.S.A.* 81:3825-3829).

However, as indicated above, the homology between the inserted gene and the endogenous gene need not be absolutely identical. Foreign homologous genes would also be subject to this same repression phenomenon. As stated, the repressive effect can occur with many different genes. It is exemplified herein, inter alia, with respect to flavonoid pathway genes.

Target Plants

As used herein, "plant" refers to either a whole plant, a plant part, a plant cell, or a group of plant cells. The class of plants which can be used in the method of the invention is generally as broad as the class of higher plants amenable to transformation techniques, including both monocotyledonous and dicotyledonous plants. It includes plants of a variety of ploidy levels, including polyploid, diploid and haploid.

Although useful in regulating expression of many plant genes, the invention is easily characterized with particular application to plants which express the flavonoid pathway genes. At least some of the flavonoid pathway genes are essentially ubiquitous in higher plants; their products are found in flowers or other plant organs (such as leaves, stems, roots, tubers, bracts, sepals, fruits, vegetables) which are colored. These colors are provided largely by anthocyanin pigments, other flavonoid pigments, copigments, or colorless flavonoids synthesized from chalcone by the plant. See Hahlbrock, supra; Harborne, (1986) *Plant Flavenoids in Biology and Medicine: Biochemical Pharmacological and Structure Activity Relationships*; Harborne, (1976) *Chemistry and Biochemistry of Plant Pigments*, (2d ed.) Vol. 1, Goodwin (Ed.) Acad. Press.

Fruit (e.g., apples, cherries, plums, grapes), vegetable (e.g., eggplant, peppers, kale, lettuce, radishes, cauliflower) or other edible plant part (e.g., potato) colors are also subject to manipulation using these techniques.

Flower colors, of course, are commonly very dependent on the activity of the flavonoid pathway genes, and thus are especially sensitive to the absolute and relative levels of expression of the flavonoid biosynthetic pathway genes. Ornamental plants and flowers are valuable commercially, and thus are typical targets of the methods herein described. Creation and selection of new coloration schemes are particularly valuable in the ornamental flower bearing plants such as chrysanthemums, carnations, roses, gerberas, lilies, geraniums, poinsettias and petunias.

Transformation

The transformation of plants in accordance with the invention may be carried out in essentially any of the various ways known to those skilled in the art of plant molecular biology. See, in general, *Methods in Enzymology* Vol. 153 ("Recombinant DNA Part D") 1987, Wu and Grossman Eds., Academic Press, incorporated herein by reference. As used herein, the term transformation means alteration of the genotype of a host plant by the introduction of a nucleic acid sequence. The nucleic acid sequence need not necessarily originate from a different source, but it will, at some point, have been external to the cell into which it is to be introduced.

In one embodiment, the foreign nucleic acid is mechanically transferred by microinjection directly into plant cells by use of micropipettes. Alternatively, the foreign nucleic acid may be transferred into the plant cell by using polyethylene glycol. This forms a precipitation complex with the genetic material that is taken up by the cell (Paszkowski et al., (1984) *EMBO J.* 3:2717-22).

In another embodiment of this invention, the introduced gene may be introduced into the plant cells by electroporation (Fromm et al., (1985) "Expression of Genes Transferred into Monocot and Dicot Plant Cells by Electroporation," *Proc. Natl Acad. Sci. U.S.A.* 82:5824, which is incorporated herein by reference). In this technique, plant protoplasts are electroporated in the presence of plasmids or nucleic acids containing the relevant genetic construct. Electrical impulses of high field strength reversibly permeabilize biomembranes allowing the introduction of the plasmids. Electroporated plant protoplasts reform the cell wall, divide, and form a plant callus. Selection of the transformed plant cells with the transformed gene can be accomplished using phenotypic markers.

Cauliflower mosaic virus (CaMV) may also be used as a vector for introducing the foreign nucleic acid into plant cells (Hohn et al., (1982) "Molecular Biology of Plant Tumors," Academic Press, New York, pp.549-560; Howell, U.S. Pat. No. 4,407,956). CaMV viral DNA genome is inserted into a parent bacterial plasmid creating a recombinant DNA molecule which can be propagated in bacteria. After cloning, the recombinant plasmid again may be cloned and further modified by introduction of the desired DNA sequence into the unique restriction site of the linker. The modified viral portion of the recombinant plasmid is then excised from the parent bacterial plasmid, and used to inoculate the plant cells or plants.

Another method of introduction of nucleic acid segments is high velocity ballistic penetration by small particles with the nucleic acid either within the matrix of small beads or particles, or on the surface (Klein et al., (1987) *Nature* 327:70-73). Although typically only a single introduction of a new nucleic acid segment is required, this method particularly provides for multiple introductions.

A preferred method of introducing the nucleic acid segments into plant cells is to infect a plant cell, an explant, a meristem or a seed with *Agrobacterium tumefaciens* transformed with the segment. Under appropriate conditions known in the art, the transformed plant cells are grown to form shoots, roots, and develop further into plants. The nucleic acid segments can be introduced into appropriate plant cells, for example, by means of the Ti plasmid of *Agrobacterium tumefaciens*. The Ti plasmid is transmitted to plant cells upon infection by *Agrobacterium tumefaciens*, and is stably integrated into the plant genome (Horsch et al., (1984) "Inheritance of Functional Foreign Genes in Plants," *Science*, 233:496–498; Fraley et al., (1983) *Proc. Natl. Acad. Sci. U.S.A.* 80:4803).

Ti plasmids contain two regions essential for the production of transformed cells. One of these, named transfer DNA (T DNA), induces tumor formation. The other, termed virulent region, is essential for the introduction of the T DNA into plants. The transfer DNA region, which transfers to the plant genome, can be increased in size by the insertion of the foreign nucleic acid sequence without its transferring ability being affected. By removing the tumor-causing genes so that they no longer interfere, the modified Ti plasmid can then be used as a vector for the transfer of the gene constructs of the invention into an appropriate plant cell, such being a "disabled Ti vector".

All plant cells which can be transformed by Agrobacterium and whole plants regenerated from the transformed cells can also be transformed according to the invention so as to produce transformed whole plants which contain the transferred foreign nucleic acid sequence.

There are presently at least three different ways to transform plant cells with Agrobacterium:

(1) co-cultivation of Agrobacterium with cultured isolated protoplasts, (2) transformation of cells or tissues with Agrobacterium, or (3) transformation of seeds, apices or meristems with Agrobacterium.

Method (1) requires an established culture system that allows culturing protoplasts and plant regeneration from cultured protoplasts.

Method (2) requires (a) that the plant cells or tissues can be transformed by Agrobacterium and (b) that the transformed cells or tissues can be induced to regenerate into whole plants.

Method (3) requires micropropagation.

In the binary system, to have infection, two plasmids are needed: a T-DNA containing plasmid and a vir plasmid. Any one of a number of T-DNA containing plasmids can be used, the only requirement is that one be able to select independently for each of the two plasmids.

After transformation of the plant cell or plant, those plant cells or plants transformed by the Ti plasmid so that the desired DNA segment is integrated can be selected by an appropriate phenotypic marker. These phenotypic markers include, but are not limited to, antibiotic resistance, herbicide resistance or visual observation. Other phenotypic markers are known in the art and may be used in this invention.

All plants from which protoplasts can be isolated and cultured to give whole regenerated plants can be transformed by the present invention so that whole plants are recovered which contain the transferred foreign gene. Some suitable plants include, for example, species from the genera Fragaria, Lotus, Medicago, Onobrychis, Trifolium, Trigonella, Vigna, Citrus, Linum, Geranium, Manihot, Daucus, Arabidopsis, Brassica, Raphanus, Sinapis, Atropa, Capsicum, Hyoscyamus, Lycopersicon, Nicotiana, Solanum, Petunia, Digitalis, Majorana, Ciohorium, Helianthus, Lactuca, Bromus, Asparagus, Antirrhinum, Hererocallis, Nemesia, Pelargonium, Panicum, Pennisetum, Ranunculus. Senecio, Salpiglossis, Cucumis, Browaalia, Glycine, Lolium, Zea, Triticum, Sorghum, and Datura.

It is known that practically all plants can be regenerated from cultured cells or tissues, including but not limited to all major cereal crop species, sugarcane, sugar beet, cotton, fruit and other trees, legumes and vegetables. Limited knowledge presently exists on whether all of these plants can be transformed by Agrobacterium. Species which are a natural plant host for Agrobacterium may be transformable in vitro. Although monocotyledonous plants, and in particular, cereals and grasses, are not natural hosts to Agrobacterium, work to transform them using Agrobacterium has also been carried out (Hooykas-Van Slogteren et al., (1984) *Nature* 311:763–764). Additional plant genera that may be transformed by Agrobacterium include Chrysanthemum, Dianthus, Gerbera, Euphorbia, Pelaronium, Ipomoea, Passiflora, Cyclamen, Malus, Prunus, Rosa, Rubus, Populus, Santalum, Allium, Lilium, Narcissus, Ananas, Arachis, Phaseolus and Pisum.

Regeneration

Normally, regeneration will be involved in obtaining a whole plant from the transformation process. The term "transgenote" refers to the immediate product of the transformation process and to resultant whole transgenic plants.

The term "regeneration" as used herein, means growing a whole plant from a plant cell, a group of plant cells, a plant part or a plant piece (e.g. from a protoplast, callus, or tissue part).

Plant regeneration from cultural protoplasts is described in Evans et al., "Protoplasts Isolation and Culture," *Handbook of Plant Cell Cultures* 1:124–176 (MacMillan Publishing Co. New York 1983); M. R. Davey, "Recent Developments in the Culture and Regeneration of Plant Protoplasts," *Protoplasts*, (1983)—Lecture Proceedings, pp.12–29, (Birkhauser, Basal 1983); P. J. Dale, "Protoplast Culture and Plant Regeneration of Cereals and Other Recalcitrant Crops," *Protoplasts* (1983)—Lecture Proceedings, pp. 31–41, (Birkhauser, Basel 1983); and H. Binding, "Regeneration of Plants," *Plant Protoplasts*, pp.21–73, (CRC Press, Boca Raton 1985).

Regeneration from protoplasts varies from species to species of plants, but generally a suspension of transformed protoplasts containing copies of the exogenous sequence is first made. In certain species embryo formation can then be induced from the protoplast suspension, to the stage of ripening and germination as natural embryos. The culture media will generally contain various amino acids and hormones, such as auxin and cytokinins. It is sometimes advantageous to add glutamic acid and proline to the medium, especially for such species as corn and alfalfa. Shoots and roots normally develop simultaneously. Efficient regeneration will depend on the medium, on the genotype, and on the history of the culture. If these three variables are controlled, then regeneration is fully reproducible and repeatable.

Regeneration also occurs from plant callus, explants, organs or parts. Transformation can be performed in the context of organ or plant part regeneration. *Methods in Enzymology*, supra: also *Methods in Enzymology*, Vol. 118; and Klee et al., (1987) *Annual Review of Plant Physiology*, 38:467-486.

In vegetatively propagated crops, the mature transgenic plants are propagated by the taking of cuttings or by tissue culture techniques to produce multiple identical plants for trialling, such as testing for production characteristics. Selection of desirable transgenotes is made and new varieties are obtained thereby, and propagated vegetatively for commercial sale.

In seed propagated crops, the mature transgenic plants are self crossed to produce a homozygous inbred plant. The inbred plant produces seed containing the gene for the newly introduced foreign gene activity level. These seeds can be grown to produce plants that would produce the selected phenotype.

The inbreds according to this invention can be used to develop new hybrids. In this method a selected inbred line is crossed with another inbred line to produce the hybrid.

Parts obtained from the regenerated plant, such as flowers, seeds, leaves, branches, fruit, and the like are covered by the invention, provided that these parts comprise cells which have been so transformed. Progeny and variants, and mutants of the regenerated plants are also included within the scope of this invention, provided that these parts comprise the introduced DNA sequences. Progeny and variants, and mutants of the regenerated plants are also included within the scope of this invention.

Vectors

Selection of an appropriate vector is relatively simple, as the constraints are minimal. The apparent minimal traits of the vector are that the desired nucleic acid sequence be introduced in a relatively intact state. Thus, any vector which will produce a plant carrying the introduced DNA sequence should be sufficient. Also, any vector which will introduce a substantially intact RNA which can ultimately be converted into a stably maintained DNA sequence should be acceptable.

Even a naked piece of DNA would be expected to be able to confer the properties of this invention, though at low efficiency. The decision as to whether to use a vector, or which vector to use, will be guided by the method of transformation selected.

If naked nucleic acid introduction methods are chosen, then the vector need be no more than the minimal nucleic acid sequences necessary to confer the desired traits, without the need for additional other sequences. Thus, the possible vectors include the Ti plasmid vectors, shuttle vectors designed merely to maximally yield high numbers of copies, episomal vectors containing minimal sequences necessary for ultimate replication once transformation has occurred, transposon vectors, homologous recombination vectors, minichromosome vectors, and viral vectors, including the possibility of RNA forms of the gene sequences. The selection of vectors and methods to construct them are commonly known to persons of ordinary skill in the art and are described in general technical references (Methods in Enzymology, supra).

However, any additional attached vector sequences which will confer resistance to degradation of the nucleic acid fragment to be introduced, which assists in the process of genomic integration or provides a means to easily select for those cells or plants which are actually, in fact, transformed are advantageous and greatly decrease the difficulty of selecting useable transgenotes.

Selection

Selection of transgenotes for further study will typically be based upon a visual assay, such as observing color changes (e.g., a white flower, variable pigment production, and uniform color pattern on flowers or irregular patterns), but may involve biochemical assays of either enzyme activity or product quantitation. Transgenotes will be grown into plants bearing the plant part of interest and the gene activities will be monitored, such as by visual appearance (for flavonoid genes) or biochemical assays (Northern blots, see, Maniatis (below); Western blots, see, Ausubel (below); enzyme assays and flavonoid compound assays, including spectroscopy, see, Harborne et al., (Eds.), (1975) *The Flavonoids*, Vols. 1 and 2, [Acad. Press]). Appropriate plants will be selected and further evaluated.

The following experimental section is offered by way of example and not by limitation.

EXPERIMENTAL

In general, preparation of plasmid DNA, restriction enzyme digestion, agarose gel electrophoresis of DNA, Southern blots, DNA ligation and bacterial transformation were carried out using standard methods. (Maniatis et al., *Molecular Cloning, A Laboratory Manual*, Cold Spring Harbor Laboratory (1982), referred to herein as "Maniatis" and hereby incorporated by reference.) Western blots and other standard molecular biology techniques are also described in Ausubel et al., (1987) *Current Protocols in Molecular Biology*, Vols. 1 and 2, and hereby incorporated by reference.

EXAMPLE 1

Plant Transformation Procedures

In Examples 1-4, reagent materials are commercially available, unless otherwise specified. Enzymes used in the cloning procedures are available from commercial sources. All restriction endonuclease reactions are carried out according to manufacturer instructions. Unless otherwise specified, the reaction conditions for other reactions are standard conditions used in the art, as described, for example, in Maniatis. Luria (L) agar and Minimal A (MinA) agar and broth are described in J. H. Miller, *Experiments in Molecular Genetics*, Cold Spring Harbor Laboratory, New York (1972) (referred to herein as "Miller" and hereby incorporated by reference). Transformations of competent *Escherichia coli* strain DH-1 were performed according to Maniatis. Plasmid DNA was prepared by alkaline extraction according to Maniatis (referred to herein as "mini-prep DNA" or "mini-prep technique"). Site specific oligonucleotide mutagenesis was carried out as described in Geisselsoder, et al., (1987) *BioTechniques* 5:(8), 786-791, except *E. coli* strain BW313 (dut,ung) was used to produce uracil—containing single stranded DNA, in vitro synthesized double stranded DNA was transformed into E. coli strain DH-1, and the Klenow fragment of DNA polymerase I was used for the second strand synthesis which was incubated overnight at room temperature.

Antibiotics are abbreviated as follows: Ap is ampicillin, Km is kanamycin, Rif is rifampicin and Tc is tetracycline. Micrograms are referred to herein as ug and milliliters are referred to as ml. Microliters are referred to as ul.

Creation of Agrobacterium Tumefaciens LBA4404/p5972 and p7506

The plasmid pcPE1 was obtained from H. Reif, Max Planck Institut, Koln. This plasmid contained a nearly full length *Petunia hybrida* chalcone synthase cDNA clone as an EcoRI fragment. (For the sequence of a chalcone synthetase gene, see, Niesbach-Klosgen et al. (1987) *J. Mol. Evolution* 26:213-225, which is incorporated herein by reference.) The construction strategy that led to the construction of the binary vectors p5972 and p7506 which were used for the reintroduction and expression of this chalcone synthase gene into target plants is shown in FIG. 1. The plasmids shown in this strategy are labeled with only the relevant restriction sites used either in the construction procedure or discussed in the text. The plasmid numbers in the middle of the circles in the figure are the actual number designations given to the plasmids in the construction strategy. The plasmid number in the lower bottom of the circles refers to the cloning vector that gave rise to the relevant clones. For example the first plasmid listed in the strategy is pcPE1. This clone resulted from a ligation of an EcoRI fragment into the commercially available cloning vector pUC18, so pcPE1 is listed in the middle of the circle and pUC18 is listed in the bottom. The restriction enzymes listed by the drawn circles indicate which enzymes were used to digest the plasmids and an arrow indicates that a ligation reaction took place. Antibiotic resistant genes that were used to select the clones are indicated inside the circles.

The EcoRI fragment containing the complete coding sequence for chalcone synthase protein was recloned into the EcoRI site of plasmid pUC119 (Viera and Messing, *In Methods in Enzymology*, 153(2) eds. Wu and Grossman, San Diego, pp.3-11, 1987) by digesting both plasmids with EcoRI, ligation, and transformation into competent E. coli strain DH-1. A plasmid which contained pUC119 and the EcoRI chalcone synthase fragment was identified by restriction mapping and was designated plasmid p6010. Plasmid p6010 was transformed into competent E. coli strain BW313 and single stranded DNA containing uracil was isolated (Viera and Messing, ibid.). A 26 base synthetic primer composed of the sequence, 5'-CTTTTTTCTAGTTAAC-CATGGTGACT-3', and a 24 base synthetic primer composed of the sequence, 5'-CTACTTAGT-GGATCCGGCTTATAT-3', were synthesized on an Applied Biosystems 381A DNA synthesizer using the solid phase phosphotriester method. The 26 base primer was used to introduce two new restriction sites, HpaI and NcoI, at the beginning of the coding sequence. The NcoI site overlapped the ATG start codon of the chalcone synthase and would be used for promoter fusions later in the construction strategy. The 24 base primer was used to introduce a BamHI site that overlapped the TAG translation stop codon and would be used later in the construction strategy to fuse the chalcone synthase gene to a poly-adenylation signal sequence. In vitro synthesized double stranded DNA (dsDNA) was synthesized using the two primers and transformed into competent E. coli strain DH-1. Ampicillin resistant colonies were screened using mini-prep DNA for new HpaI and NcoI restriction sites that mapped at the beginning of the gene and a BamHI site that mapped at the end of the gene. The plasmid that fulfilled this and further mapping criteria was designated as plasmid p5571.

The next step in the construction strategy served to fuse a 35S Cauliflower Mosaic Virus (herein called CaMV 35S promoter in the text and p35S in the figure) to the beginning of the chalcone synthase coding sequence and a poly-adenylation signal sequence to the end of the coding sequence. Plasmid pJJ2104 is described in Harpster et al., (1988) *Mol. Gen. Genet.* 212:182-190 which is incorporated herein by reference, and was used as the source of the CaMV 35S promoter and poly-adenylation signal sequence. This plasmid has a modified CaMV 35S promoter contained within a BglII and NcoI fragment. The CaMV 35S promoter within plasmid pJJ2104 is fused to the untranslated leader sequence of the photosynthetic 22L chlorophyll a/b binding protein (here in called "Cab22L") to increase transcriptional efficiency (see above reference). The poly-adenylation signal sequence is from the nopaline synthase gene (Depicker et al., (1982) *Mol. Appl. Genet.* 1(6):561-573), and is contained within a BamHI and HindIII fragment in the plasmid pJJ2104.

Plasmid p5571 DNA was isolated and cleaved to completion with BamHI and then cleaved with NcoI under conditions to give a partial, incomplete digestion of the DNA because a second NcoI site lies within the chalcone synthase coding sequence. The DNA was subjected to electrophoresis through 0.5% low melt agarose in standard Tris-Acetate EDTA buffer (described in Maniatis) with ethidium bromide at 0.5 ug/ml incorporated into the agarose. The gel was examined briefly under medium length ultraviolet light using a transilluminator (wave length 312 nm) and a band corresponding to the length (approximately 1200 base pairs) of the chalcone synthase coding sequence was excised from the gel. The gel fragment was weighed to determine the volume and brought to 0.3M sodium acetate. The equilibrated agarose was heated to 65 degrees for the 10 minutes and then extracted with an equal volume of phenol saturated with 0.1M Tris-HCl, pH 8. The aqueous phase was removed and extracted twice with a chloroform-isoamyl alcohol (24:1) mixture and the DNA was then precipitated from the aqueous solution. (All the above techniques were used according to standard conditions as described in Maniatis.) This eluted fragment was combined with plasmid pJJ2104 which was cleaved to completion with NcoI and BamHI and a ligation reaction was set up and incubated for one hour at room temperature and the reaction products subsequently transformed into competent E. coli strain DH-1. Plasmid DNA was screened with restriction enzymes to identify the appropriate plasmid containing the 35S CaMV promoter, the chalcone synthase coding sequence, and the poly-adenylation signal sequence. The plasmid p5634 was identified and subjected to restriction digestion to confirm that the plasmid was the correct one.

Two different binary vectors were used in the construction strategy. Plasmids pJJ3942 and pAGS502 are both based on the broad host range cloning vector pRK290 (Ditta et al., (1980) *Proc. Natl. Acad. Sci. U.S.A.* 77:7347-7451) and contain a Neomycin Phosphotransferase II coding sequence fused at the 5' end to a nopaline synthase promoter and at the 3' end to an octopine synthase poly-adenylation signal sequence between the left and right TDNA borders (van den Elzen et al., (1985) *Plant Mol. Biol.* 5:141–154). Plasmid pAGS502 contains a polylinker with cloning sites for BamHI, XbaI, HindIII, XhoI, EcoRI and HpaI for insertion of fragments near the TDNA right border. Plasmid pJJ3942 contains HindIII, BamHI, and HpaI as unique cloning sites near the right border. An enhancer-like sequence from the 35S CaMV promoter is contained between the BamHI and HpaI sites. This fragment spans the sequences between positions −45 and −200 of the 35S CaMV promoter to give approximately 200 bases of sequence upstream from the TATAA box.

The entire 35S CaMV promoter, the chalcone synthase coding sequence and the nos poly-adenylation signal sequence are contained within a BglII and HindIII fragment in plasmid p5634. Plasmid p5634 was digested to completion with BglII and HindIII. Two different binary vectors, pJJ3942 and pAGS502, were digested to completion with BamHI and HindIII and each was used in separate ligation reactions with plasmid p5634 digested with BglII and HindIII. The 5'-overhangs generated by the enzymes BglII and BamHI can ligated together but not recleaved by either enzyme. The ligation reactions were transformed into competent *E. coli* strain DH-1 and tetracycline resistant colonies were isolated. DNA was isolated using the mini-prep technique and screened with the appropriate restriction enzymes to isolate pJJ3942 and pAGS502 derivative plasmids that accepted the BglII and HindIII fragment. Further restriction digestions were performed to confirm the identity of the resulting plasmids. The ligation product of pJJ3942 containing the insert was designated as plasmid p5972 and the ligation product of pAGS502 containing the insert was named plasmid p7506.

Plasmids p5972 and p7506 were mobilized (transferred) separately to *Agrobacterium tumefaciens* strain LBA4404 (Ooms et al., (1981) *Gene* 14:33–50). A triparental mating procedure using *E. coli* strain DH-1 carrying p5972 or p7506 (both tetracycline resistant), *E. coli* HB101 carrying plasmid pRK2013 (kanamycin resistant) (Ditta et al., (1980) *Proc. Natl. Acad. Sci. U.S.A.* 77:7347–7351) and *A. tumefaciens* strain LBA4404 (rifampicin resistant) was set up. The two *E. coli* strains were grown up overnight on L agar (see Miller) containing the appropriate antibiotics. The *A. tumefaciens* was grown up overnight in MinA broth (see Miller) with no selection. One ml of the *A. tumefaciens* culture was pipetted into a sterile microcentrifuge tube and spun in a microcentrifuge for 2 minutes to pellet the cells. The supernatant was removed and 100 ul of fresh MinA broth was added to resuspend the pellet. A small amount of the *E. coli* cells from each of the overnight cultures was scraped off the petri dish and spread together onto a fresh L agar plate (no antibiotics). The amount of area covered by the cells was approximately 2 cm square. Each amount of *E. coli* cells was approximately equal to the amount of *A. tumefaciens* cells that was collected from 1 ml of culture. The 100 ul of resuspended *A. tumefaciens* cells was added on top of the spread *E. coli* cells and mixed to form a conjugation patch. This petri dish was incubated overnight at room temperature.

On the following day approximately one-fourth of the cells was removed from the conjugation patch and these cells were streaked for single colonies using an L agar plate containing 100 ug/ml rifampicin and 1.2 ug/ml tetracycline. The procedure was repeated four times and resulted in all of the conjugation patch streaked onto four separate plates. These plates were incubated in the dark at room temperature until colonies begin to appear (approximately 3–5 days). Isolated colonies were streaked for single colonies on MinA agar plates containing 1.2 ug/ml tetracycline. The plates were incubated for two days at 28° C. A petri dish containing MinA agar supplemented with 1.2 ug/ml tetracycline was divided into eight equal parts of a circle and eight well isolated single colonies were streaked individually onto sections of the petri dish. This plate was grown up overnight at 28° C. Three-fourths of the cells from each of the eight sections were removed from the agar using a sterile toothpick and the DNA isolated from these cells using the mini-prep technique. Each of the DNAs from these eight preparations was transformed individually into competent *E. coli* strain DH-1 and tetracycline resistant colonies were isolated. One colony from each *E. coli* transformation was grown up and the DNA isolated using the mini-prep technique. The DNA was subjected to restriction enzyme analyses to confirm that the DNA was the original binary clone that was transferred to *A. tumefaciens* LBA4404 via the triparental mating.

Plant Transformation

*Petunia hybrida* varieties: Pink Cascade was obtained from Dr. Michael Reid, Dept. of Environmental Horticulture, University of California, Davis; R18 and V26 were obtained from Dr. Anton Gerats, Dept. of Genetics, Free University, Amsterdam. *Petunia hybrida* plants were grown from surface-sterilized seed on sterile solidified agar medium of 1/10 the concentration of medium MS of Murashige supplemented with 0.5% sucrose. After germination, seedling tops were excised by cutting in the hypocotyl region and transferred to MS with 3% sucrose. Plants were maintained at 28° C. under "cool white" fluorescent light at 4–5000 lux, 16h/day.

About six weeks after planting (day 0), leaves were excised, cut with a scalpel blade into pieces about 5 mm square and inoculated with *A. tumefaciens* that had been grown overnight in MinA medium supplemented to 0.2% glucose (medium described by J. H. Miller (1972) *Experiments in Molecular Genetics*, Cold Spring Harbor Laboratory, New York) and adjusted to 0.1–0.2 $A_{550}$ units. Inoculated leaf pieces were placed on incubation medium [basal MS medium (MS+3% sucrose +B5 vitamins)+75–100uM acetosyringone, 1 mg benzyladenine (BA) per liter, and 0.2 mg indoleacetic acid (IAA)/1] for two days in a sterile transfer hood at room temperature (approx 22° C.). On day 2, 25–30 ml of liquid basal MS medium+cefotaxime (500 mg/l) was added to the plates. Plates were then swirled at 70–100 rpm for 30–60 min. Leaf pieces were transferred with the upper epidermis facing up on selection medium (basal MS+BA (1 mg/l), IAA 0.2 mg/l, vancomycin (100 mg/l)). The plates were sealed with parafilm and incubated at 24° C. under moderate light (3000–5000 lux). On day 14, leaf pieces were transferred to fresh selection medium. On day 28, calli were excised from leaf pieces and transferred to fresh selection medium and shoots were excised and transferred to hormoneless medium [basal MS+vancomycin (100 mg/l) and kanamycin (100 mg/l)]. On day 42 and following, shoots were excised from calli and transferred to hormoneless medium. After shoot elongation, shoots were excised and dipped in naphthalene acetic acid (NAA) (0.1 mg/l) for root development. After rooting, plantlets were transplanted to soil and grown in a greenhouse.

The chimeric CHS gene in p5972 and p7506 was introduced into several varieties of Petunia: (1) a hybrid variety called "Pink Cascade", (2) an inbred, R18, and (3) an inbred, V26. (See. examples 2-4)

EXAMPLE 2

Novel Derivatives of Pink Cascade Petunia

Pink Cascade produces solid pink flowers. Leaf explants from the Pink Cascade variety were transformed with p5972. Six whole plants (CS18201 through 18206) were produced. All had novel flowers. CS18201, 18203, and 18206 gave pure white petal limbs, petal tubes and anthers. CS18202 and 18205 gave flowers with a color pattern: pink wedges at the outer margin of and in the center of petal limbs with the rest of the flower pure white (some flowers on this plant were solid pure white, other flowers had this pattern). CS18204 flowers were a light, blotchy pink.

Progeny of the cross V26 x CS18202 included: 12 plants with the color of V26 x Pink Cascade and 6 plants with novel color patterns similar to the patterns of CS18202, but with smaller pigmented sectors on lower petals than upper petals in some progeny. Thus, the production of novel color patterns by the introduced gene is heritable, but the pattern itself may vary among progeny (because Pink Cascade is a hybrid variety, the progeny are genetically heterogenous).

EXAMPLE 3

Novel Derivatives of the R18 Variety Transformed with p5972

Variety R18 produces solid, pale pink flowers. Cells from the R18 variety were transformed with p5972 to produce 14 plants. Nine plants produced flowers with the normal light pink color of R18 flowers. The flowers of five plants had novel patterns. One plant gave pink radial stripes on a solid white background. Another gave mainly pure white flowers, but one flower had some pink wedge similar to wedges on CS18202. The third gave occasional white wedges at petal junctions on a solid pink background. The fourth gave a mixture of pure white flowers and pink with white radial striations (a star-like pattern). The last gave white flowers with pink wedges at the outer margins of petals.

EXAMPLE 4

Novel Derivatives of the V26 Variety Transformed with p5972 and p7506

Variety V26 produces solid, deep violet flowers. Cells from the V26 variety were transformed with p5972 to produce 37 plants. Twenty-eight plants produced flowers colored the same as the V26 parent. Seven plants had flowers with novel patterns; two plants produced pure white flowers. Three plants had pigmented wedges at petal margins similar to CS18202. One had mostly pure white flowers, but some flowers had single, small (3 mm) white spots. One plant gave flowers having a beautiful "Cossack dancer" pattern, i.e., a modified radial, star-like pattern. Two plants gave flowers with a somewhat irregular, blotchy pattern of white and purple patches; these flowers, though irregular, looked somewhat like the dancer pattern.

Cells from the V26 variety were transformed with p7506 to produce 20 plants. Seventeen plants produced flowers colored the same as the V26 parent. Three plants produced flowers with color patterns. One plant produced flowers with occasional small white spots. One plant produced one flower with a white tube, while the other flowers were similar to the V26 parent. One plant had flowers which exhibited nearly randomly distributed but sharply defined blotches.

Several transgenotes with white or patterned flowers were crossed to V26. The progeny of a white transgenote produced violet and white flowers in approximately a 1:1 ratio, as expected for a single gene. The progeny of plants with patterned flowers were also patterned or sometimes pure white. Not all plants were identical in flower color intensity or pattern. The penetrance of the flower color phenotypes was complete in the progeny populations of some transgenotes and incomplete in others, i.e., the segregation ratio of solid violet to patterned or solid white was significantly greater than 1 (for incomplete penetrance).

ANALYSES ON PETUNIA HYBRIDA TRANSGENIC PLANTS

RNA Analyses: The steady state levels of messenger RNA from both wild type plants (i.e., with an endogenous chalcone synthase gene) and transgenic plants (i.e., with an introduced 35S CaMV driven chalcone synthase gene) were analyzed in petunia petal using RNase protection analyses (protocol is titled *RNA Transcription*, available from Stratagene, 11099 North Torrey Pines Road, La Jolla, Calif.).

Petals of six different developmental stages were first harvested from V26 petunia plants and from one transgenic V26 which had white flowers (plant #21838). These stages were defined according to total petal length, degree of pigmentation, and morphology:

| Stage | Length | Pigmentation & Morphology |
|---|---|---|
| 1 | 15 mm | no pigmentation (veins only) |
| 2 | 30 | slight flush of light purple around veins |
| 3 | 40 | definite pigmentation from outer surface |
| 4 | 53 | deeper pigmentation, fully extended, still closed |
| 5 | 58 | fully pigmented, just starting to open |
| 6 | nd* | freshly mature, fully expanded |

*nd; not determined

RNA was isolated from the above described developmental stages for both wild type V26 and transgenic plant #21838. One flower of each stage except stage 1 was sufficient tissue for extracting RNA. For stage 1, eight to ten flowers were combined for the procedure. Petal tissue was frozen in liquid nitrogen and ground to a fine powder in liquid nitrogen using a pre-chilled mortar and pestle. The tissue was added to 1 ml phenol saturated with 0.1M Tris-HCl, pH 7.5 and 4 ml buffer (100 mM NaCl, 10 mM Tris-HCl, pH 7.5, 1 mM EDTA, 1% SDS) and the contents mixed. One ml of chloroform: isoamyl alcohol mixture (24:1) was added and the contents mixed again. The aqueous phase was transferred to a clean tube and extracted a second time with fresh chloroform: isoamyl alcohol mixture. The aqueous phase was transferred to a clean tube, an equal volume of 4M lithium acetate was added and the contents of the tube were placed on ice for three hours. The RNA was pelleted by centrifugation and the supernatant was removed. The pellet was dissolved in sterile water, the solution was brought to 0.3M sodium acetate and 2.5 volumes of ethanol were added to precipitate the RNA. The RNA pellet was dissolved in 100 ul of sterile water and the concentration of RNA was determined spectrophotometrically.

Five ug of RNA was used for each protection assay. A 160 nucleotide, radiolabelled anti-sense cab22L-CHS RNA was transcribed in vitro, used as a probe in the protection assays and annealed to the petal RNAs, all as described in the Stratagene protocol. After incubation with single strand specific ribonucleases RNase A and RNase T1, two different protected fragments will remain, a 94 nucleotide fragment representing the endogenous CHS mRNA and a 160 nucleotide fragment representing the introduced chalcone synthase transcript.

An autoradiogram of the RNase protection assays for all six stages of wild-type V26 petunia petal RNAs showed that the chalcone synthase protection fragment was most abundant in stage 3 and stage 4. From this experiment it was determined that the endogenous CHS mRNA is present in petals at all developmental stages examined, gradually increasing in abundance up to stage 4 and then declining to almost undetectable levels in the mature petal.

RNase protection assays on transgenic plant #21838 showed that protection fragments for both the endogenous and the introduced chalcone synthase were present. The relative levels of the endogenous chalcone synthase message followed a similar developmental profile as seen for wild-type plants; however, the overall message levels were substantially reduced, as observed by visual inspection, in each stage from the levels seen in the wild-type V26 plant. In contrast to the wild type chalcone synthase message, the chalcone synthase message from the introduced 35S CaMV promoter was present at a fairly constant low level throughout each developmental time point. This result demonstrates that the introduced CHS gene had the effect of vastly depressing the steady state level of endogenous CHS mRNA.

Protein Analyses

Antibodies were raised in a rabbit against chalcone synthase by injecting the rabbit with a fusion protein made in *E. coli*. This fusion protein consisted of wild type beta-galactosidase gene with the entire coding sequence of chalcone synthase ligated in-frame to the 3' end of beta-galactosidase (Ruther and Müller-Hill (1983) *EMBO J.* 2:(10):1791-1794). Immune antiserum from the rabbit was used in Western analyses to evaluate wild-type and transformed petunia petals. Western analysis were carried out according to manufacturer's instructions using the Proto Blot system from Promega Biotec; but similar techniques are described in Ausubel et al., (supra).

Protein extracts were prepared from purple and white segregants (described above). The same developmental stages as described above were used. Petal tissue was frozen in liquid nitrogen and then ground to a fine powder using a mortar and pestle. The frozen powder was transferred to a glass tissue homogenizer and extraction buffer (50 mM sodium phosphate buffer pH 7.0, 1 mM dithiothreotol, 0.1% Triton X-100, 1 mM EDTA) was used to homogenize the tissue. Protease inhibitors were added to final concentrations of 1 mM phenylmethysulfonyl fluoride and 0.2 mM Leupeptin. Cell debris was removed by centrifugation and the protein content of the supernatant was determined using the Bradford assay (Bradford (1976) *Anal. Biochem.* 72:248-254). Seventeen ug of protein for each sample was loaded onto an 8% polyacrylamide SDS gel.

Western analysis of purple flowered progeny showed that CHS protein was present in the petal extract of all developmental stages. The amount of CHS protein appeared to be the same for stages 1 and 2, increased in stage 3, stayed approximately the same for stages 3, 4 and 5 and decreased slightly for stage 6. Western analysis of white flowered progeny showed that, in comparison to the purple flowered progeny, barely detectable CHS protein was seen in stage 1 and appeared to be more reduced in stages 2, 3, 4, 5 and 6. These analyses showed that while CHS protein could be easily detected in protein extracts from purple flowered progeny, in protein extracts of white flowered progeny CHS protein was reduced to levels where it was barely detectable.

TLC Analysis of Flavonoids

Thin layer chromatography (TLC) was done to compare flavonoid synthesis in white versus purple flowers from progeny of the cross #21838×V26. Mitchell petunia flowers were used as a negative control for anthocyanin synthesis and a positive control for flavonoid synthesis. Flowers of three different lengths were used as follows: Mitchell (33 mm, 43 mm, 65 mm), purple (33 mm, 42 mm, 55 mm) and white (35 mm, 49 mm, 57 mm). The tubes were assayed separately from the limbs. Tissue was added to 1.0 ml of 2N HCl, allowed to stand for 2 hours at room temperature and then hydrolyzed for 20 minutes at 100° C. The supernatant was transferred to a clean tube and 200 ul of isoamyl alcohol was added. The samples were vortexed for at least five seconds and the two phases allowed to separate. Samples were spotted onto a cellulose TLC plate in four separate applications with drying between applications. Two identical plates were set up and run in two different solvent systems; acetic acid/36% HCl/water (30:3:10) and isopropanol/2N HCl (1:1). The two systems discriminate between the anthocyanins. The purple progeny flowers produced both anthocyanins and flavonols. The Mitchell flowers produced flavonols and little or no anthocyanins. The white progeny flowers produced little or no anthocyanins and little or no flavonols of the type produced by the normal purple flowers.

TLC Analysis of Anthocyanin Precursors

The marked reduction in anthocyanin accumulation in the white progeny flowers described above indicates that there is a block in the pathway for anthocyanin biosynthesis. Analysis was performed to determine at which step of the anthocyanin biosynthetic pathway the biochemical block occurred. Extracts were prepared as described above from flowers of 22838 and 21841 plants, as well as the V26 parent. As is described in Table I, the level of caffeic acid was increased significantly in 21838 and 21841 relative to the level present in V26. The level of coumaric acid was relatively unchanged.

Coumaric acid is expected to be present in V26 flowers both in the precursor pool and bound to anthocyanin (based on the Rt genotype of V26 (Heller and Forkmann, "Biosynthesis", in *The Flavonoids*, Harborne, J. B., ed., Chapman and Hall Ltd., London, 1988, pp. 399-425, and references therein). The presence of anthocyanin-bound coumaric acid complicates the analysis in terms of coumaric acid precursor levels. To determine whether the coumaric acid detected in TLC analysis above derives from the precursor or anthocyanin-bound form, a number of control petunia lines were similarly analyzed for precursors. In particular, levels of coumaric acid in the petunia line R27, which lacks the Rt gene necessary for coumaric acid linkage to anthocyanins, were compared to levels of coumaric acid in V26. As can be seen in FIG. 1, there was no detectable coumaric acid in extracts from line R27 (lanes 15 and 16), despite the presence of anthocyanin at levels comparable to V26 (band with Rf of 0.86).

To confirm that coumaric acid is generally not detected in petunia lines lacking the anthocyanin-bound form, extracts were prepared from flowers of lines W80 (mutated in the dihydroflavonol-4-reductase gene), W85 (mutated in the dihydroflavonol-4-reductase gene), W37 (mutated in the flavanone-3-hydroxylase gene) and R77 (mutated in both flavonoid 3'-hydroxylase and 3', 5'-hydroxylase genes) (Heller and Forkmann, and references therein). These mutants W37, W80, W85 and R77 produce little or no anthocyanin, but the mutational block is not at chalcone synthase (Heller and forkmann, and references therein). No coumaric acid was detected in corollas from any of these lines. This indicates that the coumaric acid detected in line V26 is not from the precursor pool, but rather is bound to anthocyanin.

The two white lines, 21838 and 21841, showed the accumulation of significantly more caffeic acid and coumaric acid as a precursor (i.e., not bound to anthocyanin) than did the parent V26, consistent with a biochemical block at the chalcone synthase step.

TABLE I

| | TLC Analysis of Petunia Lines | | | | |
|---|---|---|---|---|---|
| LINE | FLOWER | PLANT | ANTHO-CYANIN | CAF-FEIC | COU-MARIC |
| V26 | Purple | control | + | + | + |
| V26 (CHS) | White | 21838 | − | ++ | + |
| V26 (CHS) | White | 21841 | − | ++ | + |
| R27 | Red | control | + | + | − |
| R77 | Red | control | +/− | + | − |
| W37 | White | control | − | + | − |
| W80 | White | control | − | + | − |
| W85 | White | control | − | + | − |

The lines are described in the text. Symbols: −, none detected; +, detected at a level equivalent to that of line V26; ++, detected at a level significantly above that of line V26.

EXAMPLE 5

Genomic Chalcone Synthase (CHS)

Experimental procedures in Examples 5 and 6 were performed at Vrije Universiteit according to the teachings of the present invention (see, van der Krol, Mur, Beld, Mol and Stuitje, "Flavonoid Genes in Petunia hybrida: Addition of a limited number of gene copies may lead to a collapse in gene expression," Plant Cell, Vol. 2 pages 291-299 (1990)). Unless stated otherwise, standard methods were carried out in accordance with protocols as found in Maniatis and Bernard Perbal (1988), A Practical Guide to Molecular Cloning, John Wiley and Sons, New York.

A. Preparation of Transformants

VIP76 and VIP106 were derived from the Petunia hybrida V30 CHS gene A genomic clone VIP17, as described in Koes et al., (1986) Nucl. Acids Res. 14:5229-5239. Specifically, VIP76 was constructed by cloning a 7.2 kb EcoRI-SalI fragment from VIP17, containing the CHS gene A with a 0.8 kb 5' promoter region, into the EcoRI-SalI site of the binary vector BIN19 (Bevan et al., (1984) Nuc. Acids Res. 12:8711-8721). VIP106 was constructed by cloning a 8.0 kb Xba I fragment from VIP17, containing the CHS gene A with a 4.5 kb 5' promoter region, into the Xba I site of BIN19.

For transformation of Petunia hybrida VR plants (van der Krol et al., (1988) Nature 333:866-869), the binary vectors with the different gene constructs were mobilized into Agrobacterium tumefaciens strain LBA 4404 using standard triparental mating techniques (Ditta et al., (1980) Proc. Natl. Acad. Sci. U.S.A. 77:7347-7351). Transformants were obtained through the standard leaf-disc transformation method (Horsch et al., (1985) Science 227:1229-1231). Transformed Petunia hybrida VR plants were grown in a greenhouse.

B. Description of Transformants

VIP76 contains 0.8 kb of the 5' promoter region of the CHS A gene, 2.5 kb of the CHS A gene exon and intron sequences and 3.9 kb of the CHS A gene 3' flanking DNA. VIP106 contains 4.6 kb of the 5' promoter region of the CHS A gene, 2.5 kb of CHS A gene exon and intron sequences, and 0.5 o kb of the CHS A gene 3' flanking DNA. Both genomic CHS clones were introduced into petunia VR plants. Of the twenty plants regenerated which contain VIP106, one plant showed an evenly reduced pigmentation of the corolla. One of the 15 plants containing the VIP76 construct showed white flowers with small pigmented sections.

C. Messenger RNA Data

RNA was extracted from flowerbuds (stage 1-6 as defined by Koes et al., (1989) Plant Mol. Biol. 12:213-226). To average out small differences in developmental stage of the flowerbuds, five flowerbuds taken from one plant were pooled per stage. Nucleic acid isolation was performed as described by Koes et al., (1987) Plant Mol. Bio. 10:375-385.

Transcripts from VIP106 and VIP76 contain CHS gene A sequences that derive from the petunia strain V30. They can be distinguished from endogenous petunia VR CHS gene A transcripts by primer extension experiments. Primer extension experiments using $^{32}$P-labelled oligomer EL-4 (5'-dGATCAACACAGTTT-GTAGG-3') and 5 ug floral RNA (stage 4) were performed by annealing the oligomer and RNA in 10 ul 100 mM Tris HCl, 20 mM MgCl$_2$ and 100 mM KCl for 16 hours at 30° C. Then 10 ul of 1 mM dGTP, 1 mM dATP, 1 mM dTTP, 1 mM dCTP containing 5U of reverse transcriptase were added, and the solution was incubated for 30 minutes at 37° C. followed by 30 minutes at 43° C. Extension products were recovered by phenol chloroform (1:1) extraction and ethanol precipitation, and then visualized on 6% sequencing gels using sequence ladders of CHS gene A primed with the same oligonucleotide as a marker. Extension of primer EL-4 hybridizing to the first exon of CHS gene A results in one major fragment (176 nucleotides) for V30 CHS gene A mRNA, and two major fragments and one minor fragment for the VR CHS gene A mRNAs (186 and 189 nucleotides and 181 nucleotides respectively). Normal pigmented transformants containing VIP106 and VIP76 have normal expression levels of VR CHS mRNAs in pigmented floral tissue. VIP78 transformant 76-1A, in which flower pigmentation was inhibited, showed a lower than normal level of VR CHS mRNAs.

EXAMPLE 6

Dihydroflavonol Reductase (DFR)

A. Preparation of Transformants

VIP178 was constructed using a 1.3 kb EcoRI DFR cDNA fragment from clone lambda DFR-A1, which was isolated as follows. A lambda gt11 cDNA library, as described in van Tunen et al., (1988), EMBO J. 7:1257-1263, was prepared according to Young and David, (1983) Proc. Natl. Acad. Sci. U.S.A., 80:1194-1198. The library, prepared from corolla tissue of flowerbuds of Petunia hybrida line R27 (Van Tunen et al., (1988) EMBO J. 7:1257-1263) was screened with a 1.4 kb EcoRI/BamHI fragment of the pallida gene (Martin et al., (1985) EMBO J. 4:1625-1630). Fourteen clones hybridizing to this probe were purified. Thirteen of these contained an insert of nearly the same size (1.5 kb), whereas one clone contained an insert of around 1.6 kb. Sequence analysis of the 5' and 3' ends of both types of clones revealed that the smaller cDNA insert (lambda DFR-Al) was nearly full-length, whereas the larger cDNA insert had an extended 3' region and was shorter at the 5' end. Sequence analysis showed no differences between the clones. All fourteen clones showed an identical hybridization behavior, indicating that these clones represent transcripts of the same gene. The EcoRI sticky-ends were filled-in using the Klenow fragment of DNA polymerase I and dNTPs. This blunt-ended fragment was cloned into the HincII site of M13 mp7 so it could subsequently be isolated as BamHI fragment. This was cloned into the BamHI site of VIP103 (van der Krol et al., (1988) Nature 333:866-869) from which the CHS sequences had been removed. The clone which contains the BamHI DFR fragment in sense orientation to the CaMV 35-S promoter was called VIP178.

For transformation of Petunia hybrida VR plants, the binary vectors with the different gene constructs were mobilized into Agrobacterium tumefaciens strain LBA 4404 using standard triparental mating techniques (Ditta et al. (1980) Proc. Natl. Acad. Sci. U.S.A. 77:7347-7351). Transformants were obtained through the standard leaf-disc transformation method (Horsch et al. (1985) Science 227:1229-1231). Transformed petunia hybrida VR plants were grown in the greenhouse.

B. Description of Transformants

VIP178 contains the CaMV 35-S promoter, a full-length cDNA copy of the petunia R27 DFR gene and a nopaline synthase 3' tail fragment. The DFR gene construct (VIP178) was introduced into petunia VR. Of the 25 plants regenerated, 19 plants show a flower phenotype indistinguishable from that of untransformed petunia VR plants. However, six plants show a reduction in flower pigmentation in sector or ring patterns. The degree of pigmentation varies among different flowers of the same plant. For instance, flowers on transformant 178-16 are either completely pigmented or have a white corolla.

C. Messenger RNA Data

RNA was extracted from flowerbuds (stage 1-6 as defined by Koes et al., (1989) Plant Mol. Biol. 12:213-226). To average out small differences in developmental stage of the flowerbuds, five flowerbuds taken from one plant were pooled per stage. Nucleic acid isolation was performed as described by Koes et al., (1987) Plant Mol. Biol. 10:375-385. The $^{32}$P-labeled DFR antisense RNA was synthesized from the vector pTZ18U in which the full-length DFR cDNA EcoRI fragment was cloned. This probe is completely protected by the transcripts of the VIP178, while RNase protection with petunia VR DFR RNA results in multiple fragments due to sequence divergence between the DFR genes of petunia lines R27 and VR.

The RNase protection experiments permitted distinction between the DFR mRNA from the sense DFR gene construct (VIP178, transcript completely protected by the R27-DFR probe) and the petunia VR DFR mRNAs (two subfragments upon RNase protection with the R27-DFR probe). For transformants 178-16 and 178-17, the DFR mRNA steady-state level in flowerbud stage 4 resulting from expression of the transgene, together with that of the endogenous DFR, genes was analyzed. In 178-17 a high expression of the DFR transgene was observed relative to that of endogenous DFR gene(s). In pigmented floral tissue of 178-16 the same effect was noted. In contrast, a severe reduction in both the endogenous as well as the transgene DFR mRNA steady-state levels was observed in white flora tissue of transformant 178-16.

EXAMPLE 7

Novel Derivatives of the Chrysanthemum Variety Moneymaker Transformed with a Chrysanthemum CHS Sense Construct

A. Isolation of a Chrysanthemum CHS cDNA

A cDNA library was constructed in the phage λgt10 made from the commercially available chrysanthemum variety "Debonair" according to the standard methods of Hynh et al. (DNA Cloning Techniques: A Practical Approach, David Glover, ed., IRL Press, Oxford 1984, pp. 49-78, which is incorporated herein by reference). The library consisted of 5 petri plates, totalling over 200,000 recombinant lambda phage plaques. The mRNA for cDNA synthesis was prepared from flower petal tissues, as described in example 4. A hybridization probe was synthesized according to standard techniques based on highly conserved CHS sequences as described in Niesbach-Klosgen et al. (J. Molecular Evolution, 26, 213-25, 1987, which is incorporated herein by reference). The sequence of the oligonucleotide is:

5'CCTCCAGCAAAGCAACCCTGTTG-GTACATCATG 3'

Bacteriophage lambda plaques were selected on the basis of hybridization to the oligonucleotide above using standard plaque lift methodology. Hybridizing phage clones were grown up for the isolation of DNA. DNA was prepared and then digested with restriction enzyme EcoRI for subcloning into the phagemid pBLUESCRIPT KS (Strategene Cloning systems, La Jolla, Calif.). These phagemid clones were retested for hybridization with the oligonucleotide. Clones which had sequences giving a hybridization signal were subjected to sequence analysis. Using primers based on pBLUESCRIPT KS sequence, cDNA clone sequence was obtained up to about 150 bp of each end. For one such clone, 68% sequence homology was found at the 5' end of the cDNA clone, and 71% sequence homology was found at the 3' end of the cDNA clone. The amino acid homology ranged from 78% to 91% from the amino terminus to the carboxy terminus. This sequence homology is consistent with that found by Niesback-Klosgen et al. The cDNA clone with these sequences was therefore deemed to correspond to the transcript from an authentic chrysanthemum CHS gene.

B. Construction of Vectors for Introduction Into Chrysanthemum

The CHS cDNA sequence was modified to introduce an NcoI site at the start codon and a BamHI site just downstream of the stop codon, essentially as described in Example 1. The resulting plasmid was then treated with restriction enzymes NcoI and BamHI, and the fragment was ligated with an NcoI-BamHI fragment containing a promoter sequence and a polyadenylation signal sequence (plasmid pJJ2104, see Example 1). The reaction products were transformed subsequently into E. coli strain DH5α (Woodcock et al., 1989, Nuc Acids Res., 17, 3469-78), and selected for resistance to ampicillin. Bacterial colonies were picked, plasmid DNA isolated, and the resulting plasmid screened with restriction enzymes to identify the appropriate plasmid containing the 35S CaMV promoter, the chrysanthemum chalcon synthase coding sequence, and the poly-adenylation signal sequence. A plasmid was isolated with the appropriate characteristics.

To facilitate cloning in the next step, an SphI site was replaced with an EcoRI site in the plasmid above. An SphI site at the junction between the polyadenylation signal sequence and the cloning vector was replaced with an EcoRI site by first digesting with SphI, removing the 4 base-pair overhang with T4 DNA polymerase, and then ligating to EcoRI linkers. After digesting with EcoRI, a ligation reaction was performed prior to transformation into DH5α. Bacterial colonies were picked and tested for loss of the SphI site and the presence of an EcoRI site at the same location. The resulting plasmid was designated pFLG9336.

Figure 3:
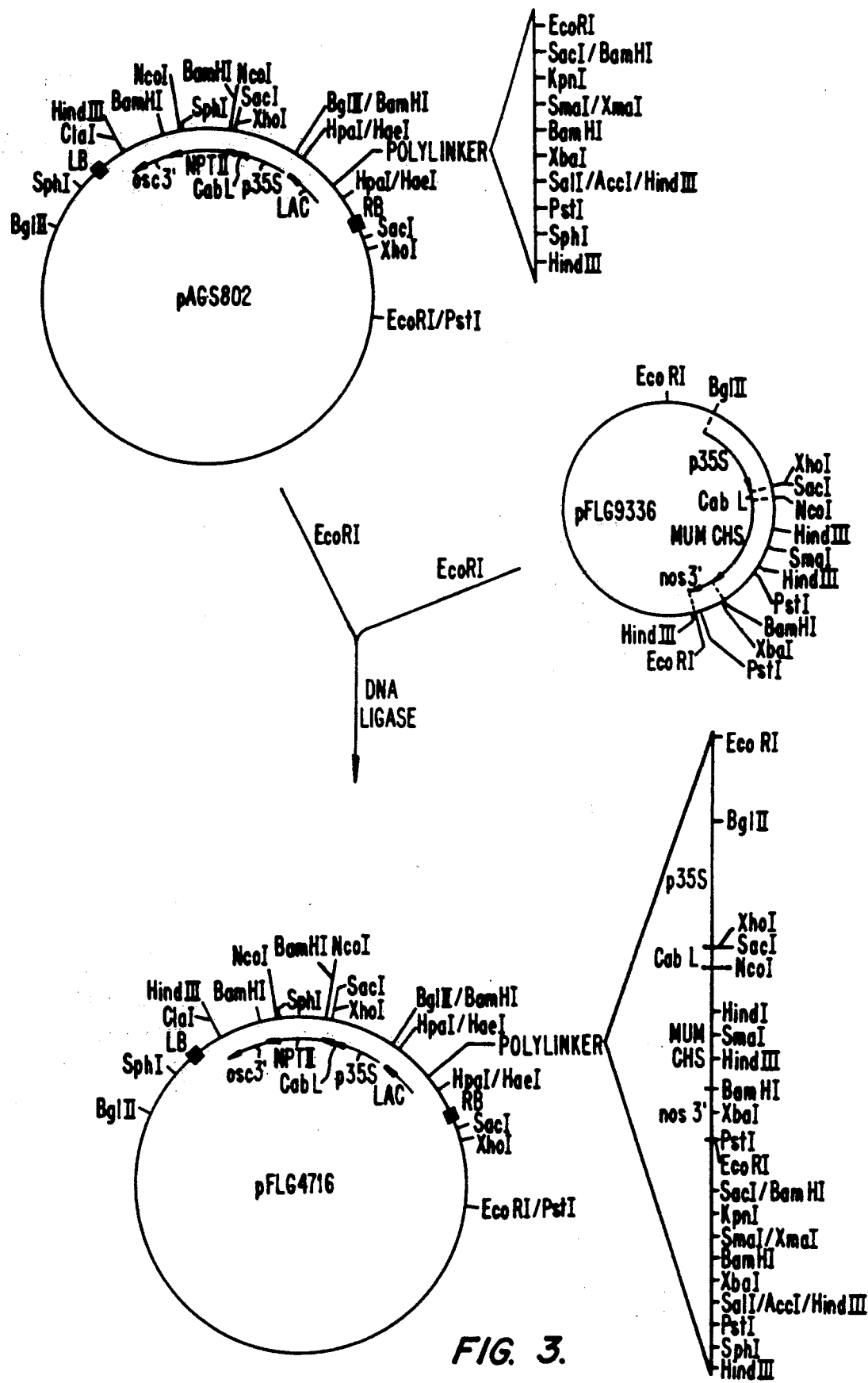
FIG. 3 shows the construction of plasmids useful in modifying chrysanthemum flower pigments.

Plasmid pAGS802 is a binary vector used for the introduction of the chrysanthemum CHS construct contained in pFLG9336. The binary vector contains left and right border regions from Agrobacterium tumefaciens T-DNA (van den Elzen et al., Plant Mol. Biol., 5, 149-54, 1985), an NPTII coding sequence (Berg at al., Proc. Natl. Acad. Sci. U.S.A., 72, 3628-32, 1975) fused at the 5' end to the CaMV 35S promoter and at the 3' end to an octopine synthase poly-adenylation signal (see Example 1), and the lacZα multiple cloning region of pUCl19. The plasmid harboring this T-DNA construct also has a minimal C01E1 replicon, obtained as the AlwnI-PvuII 180 bp fragment of pBR322 (Bolivar et al., Gene, 2, 95-113, 1977), and a Pseudomonas aeruginosa replicon, pVSI, obtained as a SacII-BamHI fragment (Stanisich et al., J. Bacteriol., 129, 1227-33, 1977). Plasmid pAGS802 has a unique EcoRI site in the lac multiple cloning region, into which was inserted the EcoRI fragment carrying the chrysanthemum CHS fusion construct of pFLG9336. After ligation reaction products were transformed into E. coli strain MJ83 (Yanish-Perron et al., 1985, Gene, 33, 103-99) and selected for gentamycin resistance, bacterial colonies were grown up for plasmid DNA isolation. Plasmid DNA was screened for the presence of the EcoRI fragment containing the CHS coding sequence construct in pAGS802, giving a plasmid designated pFLG4716 (see FIG. 3).

C. Introduction of the Chrysanthemum CHS Gene Into Chrysanthemum Variety Moneymaker Plasmid pFLG4716 was introduced into E. coli strain JM83, and then mobilized into Agrobacterium tumefaciens strain LBA4404 as described in Example 1, with gentamycin at 10 ug/ml being used as selection agent rather than tetracycline at 1.2 ug/ml. Individual transconjugant colonies were purified, and a single colony selected for chrysanthemum transformation. The colony was grown as described in Example 1, DNA was isolated, and plasmid DNA transformed into E. coli strain SK1592 (Yanish-Perron et al., 1985, Gene, 33, 103-99). The DNA was subjected to restriction enzyme analysis to confirm that the DNA retained the original structure of the binary plasmid that was transferred to A. tumefaciens LBA4404 via the triparental mating.

Alternatively, transformation was performed with A. tumefaciens strain LBA4404 containing either plasmid pAGS802 or PAGS190. Plasmid pAGS802 was described above; pASG190 is a similar derivative, except that it does not contain the lacZα fragment, and it contains a gene construct encoding hygromycin resistance (Gritz and Davies, 1983, Gene, 25, 179-88). The gene construct has the hygromycin phosphotransferase gene (HPT) coding sequence and the same transcriptional start and termination signals used for the NPTII gene.

Chrysanthemum (Dendranthema grandiflora) variety Moneymaker was obtained from Fides BV, De Lier, The Netherlands. It was maintained and propagated by placing nodal segments (7-10 mm) into Magenta GA-7 cubes (Magenta Co., Chicago) with 80 ml of an MS-based medium (MS major salts, minor salts and iron, Murashige et al., 1962, Phys. Planta., 15, 473-97), B-5 vitamins (Gamborg et al., 1968, Exp. Cell Res., 50, 148-51), 3% sucrose, 3 mM 2- (N-Morpholino) ethanesulfonic acid (MES), pH 5.7 (with KOH) which has been solidified with 0.7% Tissue Culture agar (Hazelton Biologics, In.). The in vitro plants were grown in a controlled environment room at 24.C under 16 hours illumination/day at 150-200 foot-candles of plant spectrum fluorescent illumination (Agro Lite, Philips).

Partially to fully expanded leaves and petioles from the in vitro plants were removed and placed in a few mls of sterile distilled water in a 150×20 mm petri plate. Two 4 mm wide sections, each of petiole and leaf, were made. The water was removed and the explants were then inoculated with Agrobacvterium tumefaciens strain LBA4404 containing plasmid pFLG4716 (as described above) which had been grown on Minimal A medium (Davis et al., 1950, J. Bacteriol., 60, 17-28). The explants were then removed from the excess inoculum and placed on 7.0 cm sterile Whatman #1 filter paper circles on top of incubation medium plates, specifically MS-based medium as above with 0.2% Gelrite (Scott Laboratories, Inc.), 2.0 mg/l 6-BA (6-benzylaminopurine), 1.0 mg/l NAA (2-naphthaleneacetic acid), 200 μM 3', 5'-dimethoxy- 4'-hydroxy-acetophenone (acetosyringone). The incubation medium plates were incubated at room temperature (around 22° C.) for 3 days.

Following the incubation period, explants were transferred to selection medium plates, specifically, MS-based medium solidified with 0.2% Gelrite, containing 2.9 mg/l 6-BA, 1.0 mg/l NAA, 500 mg/l Geopen (carbenicillin, Pfizer, Roerig) and 100 mg/l kanamycin sulfate. Plates were placed in clear plastic boxes and put in a controlled environment room at 24° C. with 150-200 foot-candles illumination for 16 hours/day. After 6-7 weeks, regenerated shoots were removed from the explants and placed on rooting medium, specifically, MS-based medium solidified with 0.2% Gelrite with 500 mg/l Geopen and 50 mg/l kanamycin sulfate to confirm transformation. These shoots were evaluated after 16 days for rooting in the presence of kanamycin sulfate. Rooted plantlets were transplanted to soil and grown in a greenhouse to flowering.

nia as described in a prior example above). This data is summarized in Table II.

Accumulation of caffeic and/or coumaric acid is indicative of a block at the chalcone synthase step in the pathway for flavonoid biosynthesis. This indicates that plants A, B and C, derived from transformation with a CHS gene construct, had either a complete or partial biochemical block at the chalcone synthase step.

TABLE II

| GENE CONSTRUCT | TLC Analysis of Transgenic Chrysanthemum Plants | | | | |
|---|---|---|---|---|---|
| | FLOWER COLOR | PLANT | ANTHOCYNIN | CAFFEIC | COUMARIC |
| — | pale pink | Control | + | + | + |
| pFLG4716 (CHS) | pale pink | — | + | + | + |
| pFLG4716 (CHS) | extremely light pink | C | — | + | ++ |
| pFLG4716 (CHS) | white | A,B | — | ++ | ++ |
| pAGS802 (—) | pale pink | Control | + | + | + |
| pAGS190 (—) | pale pink | Control | + | + | + |
| pAGS190 (—) | extremely light pink | D | — | + | + |

Plants A, B, C and D are described above. Symbols: —, none detected; + detected at a level equivalent to that of Moneymaker (parent); ++, detected at a level significantly above that of parent (at least 30% more).

D. Characteristics of Chrysanthemum CH Transgenic Chrysanthemums

Chrysanthemum variety Moneymaker has a pale pink color. Explants were transformed with pFLG4716 as described above to produce 133 CHS-transgenic plants. An additional 134 plants were transformed with a binary vector lacking the CHS construct. Plants were brought to flowering by subjecting them to short day conditions, created by covering the greenhouse area with black cloth for 12-13 hours each day for 80 days. Of the 267 plants 8 plants had flowers which were slightly lighter pink than the flowers of the parent, 9 plants had flowers which were yellow, and 16 had flowers which were darker pink than the flowers of the parent.

Of the 133 plants resulting from pFLG4716 transformation, the ray flowers of 2 plants were pure white (A, B), and the ray flowers of 1 plant were extremely light pink (C). No plants with white color were obtained from Moneymaker transformed with vector alone. One extremely light colored plant was obtained in a control transformation (D).

Several plants with unaltered flower color, both CHS-transformed white flower plants (A, B), the CHS-transformed extremely light colored flowering plant (C), and the control-transformed extremely light flowering control plant (D) were analyzed by thin layer chromatography for flavonoids. Ray flowers were separated from disc flowers for this analysis. The flowers from one composite flower were placed into 2.0 ml of 2N HCl, and then heated for 20 minutes at 100° C. An aliquot of the hydrolysate was transferred to an eppendorf tube and extracted with 0.2 volumes of isoamyl alcohol. Samples were run on cellulose thin layer plates as described in Example 4.

None of the plants produced flavonols; the plants with unaltered colors produced the same pattern of anthocyanins as the original Moneymaker. Plants A, B, C and D produced no detectable anthocyanins, consistent with the lack of color in the flowers. Plants A, B and C produced enhanced levels of bands with mobilities corresponding to that of caffeic acid and coumaric acid. In contrast, plant D did not accumulate additional caffeic or coumaric acids. There was no evidence of coumaric acid bound to anthocyanins (unlike V26 petu-

EXAMPLE 8

Acetolactate Synthase (ALS)

In this example, Nicotiana tabacum carrying two loci, SuRA and SuRB (Chaleff et al. (1986) Molecular Strategies for Crop Protection, UCLA Symposium on Molecular and Cellular Biology (Arntzen and Ryan, eds.), 48:15-425), which each encode the enzyme acetolactate synthase (ALS), was used in a transformation study. ALS is involved in the first common step in the biosynthesis of branched chain amino acids in plants. ALS is the site of, and is sensitive to, the action of sulfonylurea (SU) herbicides; La Rossa et al., (1984) J. Biol. Chem. 259:8753-8757. A single amino acid replacement in the ALS protein results in a herbicide resistant form of the enzyme (Lee et al. (1988) EMBO Journal 7:1241-1248); this effect can be mediated by mutation of either the SuRA or SuRB locus.

In this study, as detailed below, tobacco cells were transformed with DNA containing a deleted form of the ALS gene which would, if full length, encode a resistant form of the ALS enzyme. Homologous recombination led to several clones which were resistant (as calli) to SU as the result of replacement of the sensitive form of the ALS gene at the SuRB locus by deleted and resistant form of the ALS gene. These clones had varying numbers (one to three) of copies of the introduced fragment in addition to the substituted SuRB locus. Upon regeneration into a plant, one of the clones (containing three extra copies of the fragment) was found to have regained its sensitivity to SU. That is, the sensitivity phenotype of the SuRA locus (not homologously recombined) was manifested, and the resistance phenotype of the SuRB locus which was the site of the homologous recombination (and for which there were additional copies in the genome of the mutant fragment) was masked or suppressed. This is evidence for the repression of the ALS resistance phenotype in accordance with the method of the invention.

Experimental details and results are set forth below.

Methodology

Construction of the Targeting Plasmid

The plasmid pAGS157 contains a tobacco mutant ALS gene with three nucleotide replacements (586, 587, 1719) which give rise to the two amino acid replacements (196:pro→ala and 573:trp→leu); either one of these amino acid replacements confers herbicide resistance to the encoded ALS enzyme (Lee et al. (1988) *EMBO Journal* 7:1241-1248); pAGS167 carries the corresponding wild-type gene. These plasmids were used to construct the targeting plasmid. In vitro mutagenesis (Kunkel (1985) *Proc. Natl. Acad. Sci. U.S.A.* 82:488-492) was used to introduce a diagnostic ApaI site (AGAG-CACAC$_{1753}$→AGGGCCCAG$_{1753}$') 25 bp downstream from the 573:trp→leu mutant site in pAGS157, to form the plasmid pAGS175. This new site did not change the amino acid sequence of the protein. Subsequently, a 1.0 kb NcoI-HpaI fragment from pAGS175, containing the 196:pro→ala mutation, was replaced by the equivalent fragment from pAGS167, containing the wild-type sequence. The resulting plasmid, pAGS177, contains the single 573:trp→leu mutation and the introduced ApaI site. pAGS177 was ligated between the T-DNA borders at the BamHI site of the binary vector pAGS140 (Dean et al. (1988) *Nucleic Acids Res.* 16:7601-7617) to give the plasmid pAGS180BV. This plasmid was used as a positive control. Plant cells arising from transformation with this plasmid are resistant to hygromycin, kanamycin, and chlorsulfuron. An inactive form of the herbicide resistant ALS gene with a 1.5 kb deletion removing the promoter and the 5' 510 bp of the ALS coding region was constructed as follows. The plasmid pAGS177 was digested with ClaI and PstI and the single-strand overhangs removed by treatment with T4 DNA polymerase and dNTPs. The 1.86 kb fragment containing the 573:trp→leu mutation and the novel ApaI site was purified from an agarose gel and cloned into the HpaI site between the T-DNA borders in the binary vector pJJ2525. The resulting plasmid was named pAGS182BV and was used for the experiments. It has a total of 1.86 kb of homology to the SuRB ALS gene. The binary vectors pAGS180BV and pAGS182BV were conjugated into the Agrobacterium strain LBA4404 (Hoekema et al. (1983) *Nature* 303:179-180) by triparental mating with *E. coli* strain HB101/pRK2013 (Figurski and Helinski (1979) *Proc. Natl. Acad. U.S.A.* 76:1648-1652).

Agrobacterium Co-cultivation with Tobacco Protoplasts

The protoplasts were obtained from leaves of *N. tabaccum* var Wisconsin 38 plants propagated by nodal culture. Co-cultivation of protoplast-derived tobacco colonies with *A. tumefaciens* was carried out as described previously (van der Elzen et al. (1985) *Plant Mol. Biol.* 5:149-154). Selection for kanamycin or chlorsulfuron resistance was initiated 8 days after protoplast isolation. Co-cultured plant cells were plated on a medium containing either kanamycin (50 μg/ml) or chlorsulfuron (2 ng/ml), and this medium was replaced twice weekly. Plants were regenerated by placing colonies on the medium of Murashige and Skoog (Murashige and Skoog (1962) *Physiol. Plant* 15:473-497) containing 0.1 μg/ml NAA, 1.0 μg/ml BAP and 10 ng/ml chlorsulfuron.

Southern Analysis of Genomic DNA

Genomic DNA was isolated from selected herbicide resistant callus and shoot tissue grown in Magenta boxes, or from leaves of regenerated plants grown in the greenhouse (Dooner et al. (1985) *Mol. Gen. Genet.* 200:240-246). Approximately 10 ug of DNA was digested with 50 units of the appropriate restriction endonuclease for 2-4 hours at 37° C. Hybridization and washing were carried out as described (Lee et al. (1988) *EMBO Journal* 7:1241-1248) to high stringency. Probes were prepared either by using riboprobe vectors (Promega, Madison, Wis.) or by random priming (Boehringer Mannheim, Indianapolis, Ind.) as recommended by the manufacturers.

Segregation Analysis

Transformed plants were self-pollinated, and the resulting seed were plated on MS media (Murashige and Skoog (1962) *Physiol. Plant* 15:473-497) containing either 200 ug/ml kanamycin or 50 ng/ml chlorsulfuron. Seedlings were scored after 10 to 14 days as either sensitive or resistant depending on their ability to form roots.

RESULTS

Targeting Strategy

The targeting DNA consists of a mutant ALS gene from the SuRB locus conferring herbicide resistance which has o been inactivated by deletion of the 5' coding sequences and promoter. The resistance mutation is a trp-leu change at amino acid 573; an ApaI restriction site was introduced 25 bp downstream of this mutation to mark the targeting DNA (this sequence alteration did not change the amino acid sequence of the encoded ALS protein).

Since the coding sequences between the SuRA and SuRB genes are highly conserved (Lee et al. (1988) *EMBO Journal* 7:1241-1248), it is possible that recombination could occur at each locus, however, the products of recombination at either locus can be differentiated by their restriction digest pattern.

Transformation with the Nonfunctional Mutant ALS Gene Yields Chlorsulfuron Resistant Colonies Tobacco (cv. Wisconsin 38) protoplasts were co-cultivated with *A. tumefaciens* carrying pAGS180BV (the control plasmid) or pAGS182BV (which carries the deleted fragment from the mutant ALS gene). Following co-cultivation, protoplasts were divided and plated on chlorsulfuron (2 ng/ml) or kanamycin (50 ug/ml). Transformation with pAGS182BV produced seven chlorsulfuron resistant clones. Transformed calli and the regenerated plants derived from these calli were maintained on 10 ng/ml chlorsulfuron until transfer to the greenhouse. Each herbicide resistant transformant was tested for kanamycin resistance by transferring callus pieces to plates containing 200 ug kanamycin/ml and monitoring survival. Of the 7 chlorsulfuron resistant transformants selected, 2 (HR11 and HR15) were also kanamycin resistant.

Three Chlorsulfuron Resistant Clones Result from Homologous Recombination

To determine if the chlorsulfuron resistant clones resulted from homologous recombination or spontaneous mutation, Southern hybridizations were conducted on genomic DNA from the 7 chlorsulfuron resistant transformants. As a probe, an EcoRI-HindIII fragment was used from the SuRA gene which spans the introduced mutations and extends 450 bp in the 5' and 750 bp in the 3' direction.

After genomic DNA is digested with NcoI and ApaI, the two endogenous ALS genes, SuRA and SuRB, give rise to hybridizing bands of 4.7 kb and 2.0 kb. Homologous recombination between the pAGS182BV DNA and the ALS genes at SuRA or SuRB should result in the appearance of two new bands of 1.2 kb and 0.8 kb.

In each instance the hybridization pattern for DNA isolated from three independent chlorsulfuron resistant transformants (HR11, HR14 and HR15) digested with NcoI and ApaI showed the bands predicted if homologous recombination had occurred. The other four chlorsulfuron resistant transformants had hybridization patterns which were identical to untransformed tobacco (data not shown); hence, it is presumed they have arisen from spontaneous mutation at the SuRA or SuRB loci. The Southern hybridization patterns for DNA from HR11, HR14 and HR15 showed the 1.2 kb and 0.8 kb bands predicted to result from homologous recombination at the SuR loci. In DNA from HR11 and HR14, there appeared to be no ALS hybridizing bands other than those attributed to homologous recombination, suggesting additional T-DNA random insertion events had not occurred. In the plant HR15 three extra hybridizing ALS bands occurred, suggesting three additional insertions of T-DNA in this transformant.

Southern hybridization was also carried out following digestion of DNA with SpeI, which cuts in the genomic sequences flanking the SuR loci. When tobacco genomic DNA digested with SpeI and ApaI, the endogenous ALS genes should give rise to hybridizing bands of 10 kb and 3.4 kb. Homologous recombination between pAGS182BV DNA and SuRA should result in new 5.4 kb and 0.8 kb bands, while recombination at SuRB should result in hybridizing fragments of 2.6 kb and 0.8 kb.

Hybridization bands were analyzed for the genomic DNA isolated from regenerated plants after digestion with SpeI and ApaI. The 2.6 kb band predicted following homologous recombination at SuRB appeared only in DNA from the putative recombinants HR11, HR14 and HR15. The other hybridizing fragments in these DNAs apparently represent the SpeI-ApaI fragments generated from the random insertion of the T-DNA carrying the targeting ALS gene into the genome. As expected, based on the NcoI-ApaI hybridization patterns, HR15 had at least two other hybridizing bands in the SpeI-ApaI digestions. An additional band was also seen in HR11 DNA, suggesting at least one T-DNA random insertion. These data are consistent with the observation that HR11 and HR15 are also kanamycin resistant, indicating that they contain a functional NPTII gene. The results from SpeI-ApaI hybridizations show that the novel ApaI restriction site marker in the targeting DNA is now linked to a restriction site outside the SuRB gene.

Chlorsulfuron Resistance Segregates as a Single Mendelian Gene in the Recombinant Plants HR11 and HR14

The results of genetic analysis of the transformants HR11, HR14 and HR15 are summarized below. The segregation of chlorsulfuron resistance to sensitivity in the progeny from self-pollinated HR14 was consistent with a ratio of 3:1 resistant:sensitive, indicating a single dominant locus for chlorsulfuron resistance. All seed derived from HR14 were kanamycin sensitive. Progeny from self-pollinated HR11 gave a ratio of chlorsulfuron resistance to sensitivity consistent with either a 3:1 or a 2:1 ratio, indicating a single Mendelian locus with the possibility of partial penetrance or homozygous lethality. The segregation of kanamycin resistance in these progeny was consistent with a single locus for kanamycin resistance. When grown on media containing both kanamycin and chlorsulfuron, these progeny segregated 9:7 resistant:sensitive. This suggested that the markers for kanamycin resistance and chlorsulfuron resistance were not linked. Progeny from HR15 were not chlorsulfuron resistant (0/500 seed). On kanamycin the ratio of resistant to sensitive progeny was consistent with a 63:1 ratio, indicating the presence of three independent loci for kanamycin resistance.

Overall, the observed phenotype of the HR15 plant is consistent with the introduced resistant fragment of the ALS gene, which replaced the sensitive form of the gene at the SuRB locus, being suppressed by the additional three other copies which occur (in a non-expressed state) in the genome. This suppression was not immediate upon the introduction of the resistant ALS genes since the callus from which HR15 was derived was herbicide resistant; however, with the ongoing cell division and plant regeneration, the herbicide resistant phenotype was suppressed.

EXAMPLE 9

Novel Derivatives of Plants with Modified Production of Plant Oils

The coding region of the stearyl desaturase (SD) gene is isolated in the same manner as described above in Example 1 for the chalcone synthase gene, and using information known in the art about lipid biosynthetic pathways at the genetic level (see, e.g., citations on same above). The SD gene is modified to contain isolated flanking restriction sites for introduction into the pJJ2104 plasmid. This provides a genetic construct having a modified 35S Cauliflower Mosaic Virus promoter in the correct orientation to produce a sense transcript having a poly-adenylation signal from the nopaline synthase gene. A modified photosynthetic 22L chlorophyll a/b leader sequence is also included as described above.

The new construct is checked to verify the correct orientation and vector content. A triparental mating, as described above in Example 1, is then performed using corresponding vector constructs and strains for the SD gene.

Plant transformation with *A. tumefaciens* clones is performed as described in Example 1. After transgenote cells are generated, whole plants are regenerated as described. Screening of plants exhibiting desired modified oil contents is performed by assaying the oil or lipid production of the transgenote plants on HPLC columns or other methods in accordance with standard procedures.

EXAMPLE 10

Novel Derivatives of Plants with Altered Production of Sugars or Carbohydrates

An isolated petunia starch synthase gene is substituted for the chalcone synthase gene in the procedure described in Examples 1 and 8. The procedure is performed essentially as described except for the screening. A standard iodine based starch assay or other assay for starch content of a biological sample is used to determine, for selection, the plant transgenotes exhibiting a modified starch content.

All publications are herein incorporated by reference to the same extent as if each individual publication or patent application was specifically and individually indicated to be incorporated by reference. The invention now being fully described, it will be apparent to one of ordinary skill in the art that many changes and modifications can be made thereto without departing from the spirit or scope of the claims.

What is claimed is:

1. A method for producing a plant exhibiting at least one modified phenotypic trait by suppressing expression of an endogenous gene in the plant, said method comprising the steps of:

transforming plant cells with a polynucleotide to produce transgenote cells, the polynucleotide comprising a promoter operably linked to a DNA segment such that transcripts of the segment are produced in the sense orientation in the transgenote cells which segment transcripts have at least 65% sequence identity to transcripts of said endogenous gene and are effective to suppress expression of said endogenous gene in said plant cell;

growing plants from one or more of said transgenote cells, wherein production of mRNA encoded by the endogenous gene is reduced in one or more of the plants; and selecting a plant exhibiting said modified phenotypic trait.

2. A method of claim 1, wherein said plant is a flowering plant.

3. A method of claim 1, wherein the segment encodes a full-length protein.

4. A method of claim 1, wherein the segment encodes a flavonoid metabolic pathway protein.

5. A method of claim 1, wherein the segment encodes a protein in the fatty acid biosynthetic pathway.

6. A method of claim 1, wherein the segment encodes a protein in the sugar to starch biosynthetic pathway.

7. A method of claim 1, wherein said promoter is a constitutive promoter.

8. A method of claim 1, wherein a transcript of the segment in the transgenote cells is identical to a transcript of the endogenous gene sequence in the transgenote cells.

9. A method of claim 1, wherein said polynucleotide is in a DNA vector.

10. A method for reducing production of a protein product of an endogenous gene in a plant, said protein affecting a phenotypic trait in the plant, said method comprising the steps of:

growing plants from a plant cell transformed with a DNA segment under operational control of a promoter, wherein transcripts of the DNA segment are in the sense orientation produced which are substantially homologous to transcripts of an endogenous gene encoding the protein, and wherein production of the protein is reduced; and identifying a plant that exhibits a phenotypic change by screening the plants for modification of the phenotypic trait.

11. A method of claim 10, wherein said plant cells are transformed with a Ti plasmid vector comprising said DNA segment.

12. A method of claim 11, wherein said vector comprises a constitutive promoter.

13. A method of claim 10, wherein said promoter is heterologous to said plant.

14. A method of claim 10, wherein said segment encodes a flavonoid metabolic pathway gene.

15. A method of claim 10, wherein said plant is a dicotyledonous plant.

16. A method of claim 10, wherein said plant produces flowers.

17. A method of claim 10, wherein said plant is selected from the group consisting of the genus Petunia or chrysanthemum.

18. A method for modifying the coloration of chrysanthemum flowers comprising altering flower pigment production by transforming a chrysanthemum cell with a chalcone synthase gene or gene segment contained in a disabled Ti plasmid of *Agrobacterium tumefaciens*, wherein said chalcone synthase gene is operably linked to a promoter.

19. A plant of the genus chrysanthemum produced by the method of either of claims 1 or 10 exhibiting altered flower coloration, said plant comprising plant cells transformed with a sequence which is transcribed into an RNA sequence substantially homologous to an endogenous flavonoid biosynthetic pathway gene transcript.

20. A plant of claim 19, wherein said plant cells are transformed with a Ti plasmid vector.

21. A plant of claim 19, wherein said RNA sequence is at least about 500 bp in length and encodes a chalcone synthase protein fragment.

22. A method of claim 1, wherein said transcripts of the segment produced in the transgenote have greater than about 80% sequence identity to said transcripts of said endogenous gene.

23. A method of claim 1, wherein a plant exhibiting the modified phenotypic trait is selected visually.

24. A method of claim 1, wherein a plant is selected by identifying reduced levels of mRNA encoded by the endogenous gene.

25. A method according to claim 10, wherein the transcripts of the DNA segment correspond to a full length transcript of the endogenous gene.

26. A method of modifying a plant cell phenotype by reducing the level of mRNA encoded by an endogenous gene in the plant cell, said method comprising:

growing plant cells transformed with a polynucleotide comprising a transcribable DNA segment located downstream from an operably linked promoter, whereby the segment is transcribed in the cell in the sense orientation, wherein the transcribed DNA segment has a sequence complementary to the mRNA endoded by the endogenous gene and whereby transcription of the DNA segment is effective to reduce the level of mRNA transcribed by said endogenous gene; and screening the cells for the modified phenotype.

27. A method according to claim 26, wherein the promoter is constitutive.

28. A method according to claim 26, wherein the endogenous gene is dihydroflavonal reductase.

29. A method according to claim 26, wherein the plant cell is a dicot plant cell.

30. A method according to claim 26, wherein the plant cell is a tobacco protoplast.

31. A method according to claim 26, wherein the transcribable segment encodes an herbicide resistant tobacco acetolactate synthase gene.

* * * * *

UNITED STATES PATENT AND TRADEMARK OFFICE
CERTIFICATE OF CORRECTION

PATENT NO. : 5,283,184

DATED : February 1, 1994

INVENTOR(S) : Richard A. Jorgensen; Carolyn A. Napoli

It is certified that error appears in the above-indentified patent and that said Letters Patent is hereby corrected as shown below:

Column 8, line 51, delete "Caltivar" and insert --Cultivar--.

Column 20, line 2, delete "i.2" and insert --1.2--.

Column 26, line 27, delete "0.5 o kb" and insert --0.5 kb--.

Column 29, line 51, delete "pUCI19" and insert --pUC119--.

Column 34, line 23, delete "has o been" and insert --has been--.

Column 37, line 53, delete "in the sense orientation produced" and insert "produced in the sense orientation".

Column 37, line 66, delete "plant" and insert --DNA segment--.

Column 38, line 2, delete "gene" and insert --enzyme--.

Signed and Sealed this

First Day of November, 1994

Attest:

Attesting Officer

BRUCE LEHMAN

Commissioner of Patents and Trademarks

UNITED STATES PATENT AND TRADEMARK OFFICE
CERTIFICATE OF CORRECTION

PATENT NO. : 5,283,184
DATED : February 1, 1994
INVENTOR(S) : Jorgensen; Richard A.; Napoli, Carolyn A.

Page 1 of 1

It is certified that error appears in the above-identified patent and that said Letters Patent is hereby corrected as shown below:

Title page,
After "The portion of the term of this patent subsequent to", "July 27, 2010" should be replaced with -- March 30, 2009 --.

Signed and Sealed this

Twenty-eighth Day of August, 2001

*Attest:*

*Attesting Officer*

NICHOLAS P. GODICI
*Acting Director of the United States Patent and Trademark Office*